US006214564B1

(12) United States Patent
Rodan et al.

(10) Patent No.: US 6,214,564 B1
(45) Date of Patent: Apr. 10, 2001

(54) METHOD OF IDENTIFYING MODULATORS OF PROTEIN TYROSINE PHOSPHATASE ACTIVITY

(75) Inventors: Gideon A. Rodan, Bryn Mawr; Su Jane Rutledge, East Greenville; Azriel Schmidt, Bryn Mawr, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/158,657

(22) Filed: Sep. 22, 1998

Related U.S. Application Data

(62) Division of application No. 08/800,825, filed on Feb. 14, 1997, now Pat. No. 5,866,397, which is a division of application No. 08/348,006, filed on Dec. 1, 1994, now Pat. No. 5,658,756, which is a continuation-in-part of application No. 08/122,032, filed on Sep. 14, 1993, now abandoned.

(51) Int. Cl.$^7$ ........................ G01N 33/53; G01N 33/567; C12P 21/06; C12N 15/00; C07K 1/00

(52) U.S. Cl. ...................... 435/7.1; 435/7.2; 435/252.3; 435/325; 435/471; 435/320.1; 435/69.1; 435/70.1; 435/71.1; 435/71.2; 530/350; 536/23.2

(58) Field of Search ................................ 435/7.2, 252.3, 435/320.1, 69.1, 7.1, 70.1, 71.1, 71.2, 325, 471; 530/350; 536/23.2

(56) References Cited

PUBLICATIONS

Rudinger J. et al. Characteristics of the amino acids as components of a peptide hormone sequence. in Peptide Hormones. pp. 1–7. Edited by Parsons, JA; Mill Hill, London, 1976.*
Fong TM.et al. Localization of agonist and antagonist binding domains of the human heurokinin–1 receptor. J. Biol. Chem. 267:36, pp. 25664–25667, 1992.*
Tonks NK.and Charbonneau H. Protein tyrosine dephosphorylation and signal transduction. TIBS. 14, pp. 497–500, 1989.*
Hunter T. Protein–tyrosine phosphatases: the other side of the coin. Cell. 58, pp. 1013–1016, 1989.*
Fischer EH.et al. Protein tyrosine phosphatases: a diverse family of intracellular and transmembrane enzymes. Science. 253, pp. 401–406, 1991.*
Pot DA.et al. Cloning, bacterial expression, purification and characterization of the cytoplasmic domain of rat LAR, a receptor–like protein tyrosine phosphatase. J. Biol. Chem. 266:29, pp. 19688–19696, 1991.*
Yi et al. "Identification of Novel Protein Tyrosine Phosphatases of Hematopoietic Cells by Polymerase Chain Reaction Amplification", Blood, vol. 78, No. 9, Nov. 1991; pp 2222–2228.

Wergedal et al. "Human Bone Cells Contain a Fluoride Sensitive Acid Phosphatase: Evidence that this Enzyme Functions at Neutral pH as a Phosphotyrosyl Protein Phosphatase": Clin. Biochem. vol. 25, Feb. 1992: pp 47–53.
Kaplan et al. "Cloning of three human tyrosine phosphatases reveals a multigene family of receptor–linked protein–tyrosine–phosphatases expressed in brain", Proc. Natl. Acad. Sci. vol. 87. pp 7000–7004 1990.
Chernoff et al. "Cloning of a cDNA for a major human protein–tyrosine–phosphatase", Proc. Natl. Acad. Sci, vol. 87, pp 2735–2739, Apr. 1990.
Krueger et al. "A human transmembrane protein tyrosine phosphatase, PTPζ, is expressed in bring and has an N–terminal receptor domain homologous to carbonic anhydrases", Proc. Natl. Acad. Sci., vol. 89, pp 7417–7421, Aug. 1992.
Hashimoto et al. "Insulin receptor and epidermal growth factor receptor dephosphorylation by three major rat liver protein–tyrosine phosphatases expressed in a recombinant bacterial system". J. Biochem. vol. 284 (1992) pp 569–572.
Lau et al. "Purification and Characterization of an Acid Phosphatase that Displays Phosphotyrosyl protein Phosphatase Activity from Bovine Cortical Bone Matrix", J. of Biol. Chem. No. 3. pp 1389–1397, 1987.
Lau et al. "Phosphotyrosyl protein phosphatases", Biochem. (1989) vol. 257, pp 23–26.
Mizuno et al. "Developmental regulation of gene expression for the MPTpδ isoforms in the central nervous system and the immune system", FEBS Letters 355 (1994) 223–228.
Yan et al. "A Novel Receptor Tyrosine Phosphatase–σ That is Highly Expressed in the Nervous System", Journal of Biological Chemistry, vol. 268, No. 33, pp 24880–24886 (1993).
Schmidt et al. "Identification of an Osteoclast Specific Protein Tyrosine Phosphatase and its Potential Role in Osteoclast Fusion and Bone Resorption", Biochemical Journal, vol. 8, Supp 1. pp S144. Abs 111. 1993.
Krueger et al. "Structural diversity and evolution of human receptor like protein tyrosine phosphatases ", EMBO Journal vol. 9, p 3241–3252, 1990.
Streuli et al., "A New Member of the Immunoglobulin Superfamily That Has a Cytoplasmic Region Homologous to the Leukocyte Common Antigen", J. of Exp. Med. vol. 168, pp 1523–1530. 1988.

(List continued on next page.)

Primary Examiner—Gary L. Kunz
Assistant Examiner—Robert S. Landsman
(74) Attorney, Agent, or Firm—Sheldon O. Heber; Jack L. Tribble

(57) ABSTRACT

A human protein tyrosine phosphatase (PTP) has been identified and its cDNA has been isolated. This PTP, denoted PTP-OB, has a receptor-like three dimensional structure and is present in osteoblasts. PTP-OB is involved in osteoblast differentiation, and modulators of PTP-OB activity in turn modulate osteoblast differentiation, osteoclast differentiation and osteoclast activity.

6 Claims, 12 Drawing Sheets

OTHER PUBLICATIONS

Endo et al, "Human Protein Tyrosine Phosphatase–σ: Alternative Splicing and Inhibition by Bisphosphonates", J. Bone and Mineral Research, vol. 11, pp 535–543, 1996.

Pulido et al. The LAR/PTP /PTP Subfamily of Transmembrane Protein–Tyrosine–Phosphatases: Multiple Human LAR, PTP , and PTO isoforms are expressed in a Tissue–Specific Manner and Associate with the LAR–Interaction Protein Proc. Natl. Acad. Sci., vol. 92, pp 11686–11690, 1995.

Lau, K.–H. William et al., Vanadate Stimulates Bone Cell Proliferation and Bone Collagen Synthesis in Vitro*, Endocrinology, vol. 123, No. 6, pp 2858–2867, 1988.

Krieger, N. S. et al., Inhibition of Stimulated Bone Resorption by Vanadate*, Endocrinology, vol. 113 No. 1, pp 324–328, 1983.

* cited by examiner

FIG. 11

```
  1  MEPFCPLLLA SFSLSLARAG QGNDTIPTES NWTSTTAGPP DPGASQPLLI
 51  WLLLPLLLL  FLLAAYFFRF RKQRKAVVSS NDKKMPNGIL EEQEQQRVML
101  LSRSPSGPKK FFPIPVEHLE EEIRVRSADD CKRFREEFNS LPSGHIQGTF
151  ELANKEENRE KNRYPNILPN DHCRVILSQV DGIPCSDYIN ASYIDGYKEK
201  NKFIAAQGPK QETVNDFWRM VMEQRSATIV MLTNLKERKE EKCYQYWPDQ
251  GCWTYGNIRV CVEDCVVLVD YTIRKFCIHP QLPDSCKAPR LVSQLHFTSW
301  PDFGVPFTPI GMLKFLKKVK TLNPSHAGPI VVHCSAGVGR TGTFIVIDAM
351  MDMIHSEQKV DVFEFVSRIR NQRPQMVQTD VQYTFIYQAL LEYYLYGDTE
401  LDVSSLERHL QTLHSTATHF DKIGLEEEFR KLTNVRIMKE NMRTGNLPAN
451  MKKARVIQII PYDFNRVILS MKRGQEFTDY INASFIDGYR QKDYFMATQG
501  PLAHTVEDFW RMVWEWKSHT IVMLTEVQER EQDKCYQYWP TEGSVTHGDI
551  TIEIKSDTLS EAISVRDFLV TFKQPLARQE EQVRMVRQFH FHGWPEVGIP
601  AEGKGMIDLI AAVQKQQQQT GNHPITVHCS AGAGRTGTFI ALSNILERVK
651  AEGLLDVFQA VKSLRLQRPH MVQTLEQYEF CYKVVQDFID IFSDYANFK
                                                        (SEQ ID NO. 7)
```

METHOD OF IDENTIFYING MODULATORS OF PROTEIN TYROSINE PHOSPHATASE ACTIVITY

RELATED APPLICATIONS

This is a division of Ser. No. 08/800,825, filed Feb. 14, 1997, now U.S. Pat. No. 5,866,397, which is a division of Ser. No. 08/348,006, filed Dec. 1, 1994, now U.S. Pat. No. 5,658,756, which is a continuation-in-part of Ser. No. 08/122,032, filed Sep. 14, 1993, now abandoned.

BACKGROUND OF THE INVENTION

Protein tyrosine phosphorylation plays an important role in the regulation of cellular signal transduction, cell growth and differentiation. The level of tyrosine phosphorylation is controlled by the equilibrium of the activities of the protein tyrosine kinases (PTK) and protein tyrosine phosphatases (PTP) (Cantley, L. C. et al., 1991, Cell, 64, pp.281–302; Fischer, E. H. et al., 1991, Science, 253, pp.401–406; Alexander, D. R. and Cantrell, D. A., 1989, Immunol. Today, 10, pp.200–205; Tonks, N. K. and Charbonneau, H., 1989, Trends Biochem. Sci., 14, pp.497–500; Saito, H. and Streuli, M. 1991. Cell Growth And Differentiation, 2, pp.59–65; Gautier, J. et al., 1991, Cell, 67, pp.197–211; Zheng, X. M. et al., Nature, 359, pp.336–339). It is well documented that tyrosine kinase activities play an important role in the growth and the differentiation of bone cells. M-CSF and its receptor c-fms were shown to be crucial in osteoclast development. Recently Soriano et al. reported that disruption of c-src proto-oncogene, by homologous recombination, induced osteoporosis, that is characterized by the reduction of bone resorption due to impairment of osteoclastic function (Soriano, P. et al., 1991, Cell, 64, pp.693–702; Boyce, B. F. et al., 1992, J.Clin.Invest., 90, pp.1622–1627). In both in vivo and in vitro experiments it was demonstrated that FGF, IGF-I and IGF-II are important for the osteoblast functions. These findings suggest that the control of tyrosine phosphorylation is clearly important for bone cells.

As mentioned above, protein tyrosine phosphorylation is lightly balanced by the opposing actions of protein tyrosine kinases and protein tyrosine phosphatases. Treatment of bone cells with orthovanadate, a PTPase inhibitor, resulted in the stimulation of cell proliferation and the synthesis of bone collagen (Lau et al. Endocrinology, 1988, 123 pp. 2858–2867). In organ cultures, vanadate treatment inhibited the stimulation of bone resorption induced by treatment with PTH (Krieger and Tashjian, Endocrinology, 1983, 113. pp. 324–328). Taken together, these findings suggest that PTPases play an important function in bone cells.

SUMMARY OF THE DISCLOSURE

The polymerase chain reaction methodology was used to identify cDNA molecules for several PTPases in bone cells. One of these cDNA clones, named PTP-OB, encoded a novel member of the protein tyrosine phosphatase family. From human cDNA libraries, the entire open reading frame-encoding DNA was cloned for that protein. PTP-OB is composed of 1911 amino acid residues. Sequence analysis revealed two regions of hydrophobic amino acid residues that comprise a putative signal peptide and transmembrane domain, thus indicating PTP-OB as a receptor-like PTPase. The amino acid sequence of PTP-OB shows the best similarity to LAR and LAR related PTPases. As described for LAR, three immunoglobulin-like and eight fibronectin type III-like domains can be identified in the extracellular domain, and two tandem repeats of PTPase domains in the cytoplasmic region. The cDNA clones isolated from human brain library contained a deletion of 1227 bp that maintained the open reading frame, but coded for an extracellular region that was shorter by 409 amino acid residues and one with one amino acid substitution. Hybridization experiments revealed that PTP-OB was expressed as a 7.3 kilo base (kb) mRNA in both bone and brain tissues. The tissue distribution of PTP-OB transcript suggested that this receptor-like PTPase is involved in the growth and differentiation of osteoblasts and brain cells.

BRIEF DESCRIPTION OF THE DRAWINGS

FIG. 11. The amino acid sequence of the mouse mPTPε (SEQ.ID.NO.: 7) is and has the structure of a transmembrane protein; the signal peptide and transmembrane regions are underlined, and the conserved PTP regions are boxed.

DETAILED DESCRIPTION OF THE INVENTION

Figure 1:
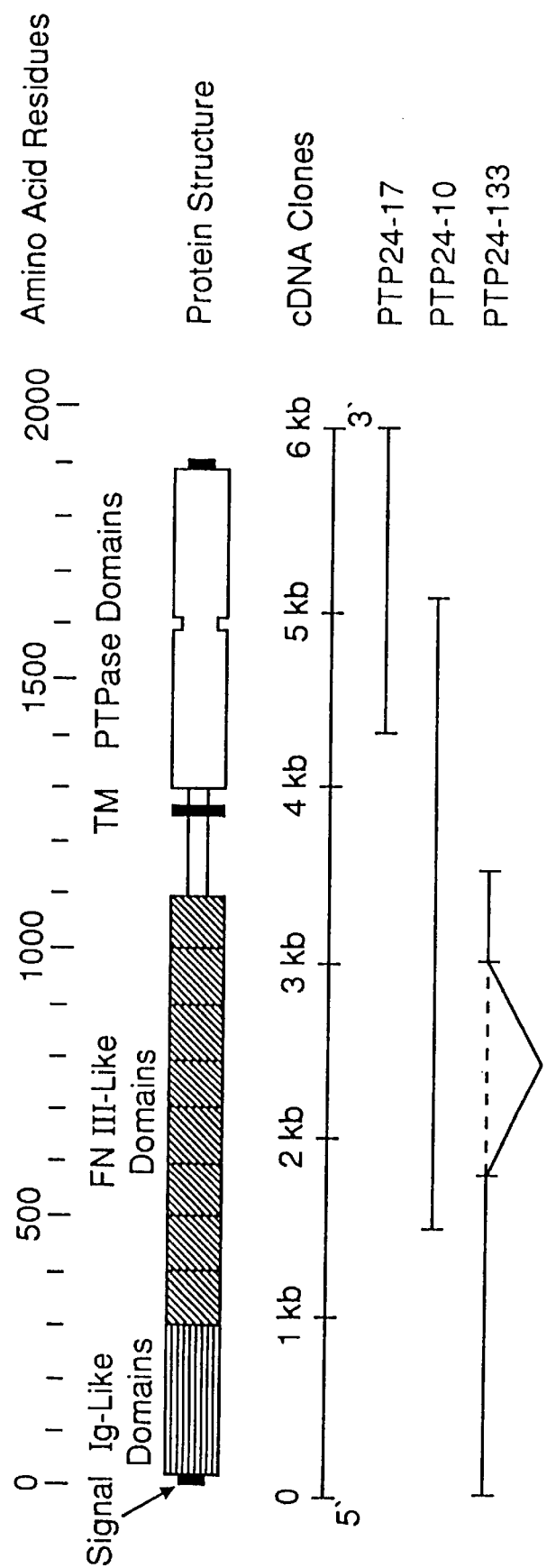
FIG. 1. Schematic structure of PTP-OB overlapping cDNA clones were isolated from various human cDNA libraries: PTP-OB-17 from human fetal lung library, PTP-OB-10 human giant cell tumor library and PTP-OB-133 from human fetal brain library are shown, depicting the extracellular region with the signal peptide, the immunoglobulin-like domains (Ig-like), the fibronectin (FN) type III-like domains, the transmembrane (TM) domain and the cytoplasmic region with the PTPase domains.

The present invention relates to cDNA encoding a novel protein tyrosine phosphatase termed PTP-OB. The present invention is also related to recombinant host cells which express the cloned PTP-OB-encoding DNA contained in a recombinant expression plasmid. The present invention is also related to a method for the screening of substances which modulate PTP-OB protein activity. The DNA of the present invention is isolated from PTP-OB producing cells. PTP-OB, as used herein, refers to a protein tyrosine phosphatase which is specifically expressed in bone and brain cells. The present invention also relates to a unique protein tyrosine phosphatase protein, also described as PTP-OB, which is isolated from PTP-OB producing cells. PTP-OB protein, as used herein, refers to a protein tyrosine phosphatase protein which is specifically produced by bone and brain cells.

Mammalian cells capable of producing PTP-OB include, but are not limited to, cells derived from bone such as MB1.8 and brain cells such as U340. Transformed mammalian cell lines which produce PTP-OB include, but are not limited to, NIH 3T3 cells. The preferred cells for the present invention include normal human HELA, NIH 3T3, U2, and CHO cells and the most preferred cells are human 293 cells.

Other cells and cell lines may also be suitable for use to isolate PTP-OB cDNA. Selection of suitable cells may be done by screening for PTP-OB produced by the cells. Methods for detecting PTP-OB activity are well known in the art (in: Maniatis, T., Fritsch, E. F., Sambrook, J., Molecular Cloning: A Laboratory Manual Cold Spring Harbor Laboratory, Cold Spring Harbor, N.Y., 1982) and measure the level of PTP-OB RNA produced by the cells. Cells which possess PTP-OB activity in this assay may be suitable for the isolation of PTP-OB cDNA.

Any of a variety of procedures may be used to clone PTP-OB cDNA. These methods include, but are not limited to, direct functional expression of the PTP-OB cDNA following the construction of an PTP-OB-containing cDNA library in an appropriate expression vector system. Another method is to screen an PTP-OB-containing cDNA library constructed in a bacteriophage or plasmid shuttle vector with a labelled oligonucleotide probe designed from the amino acid sequence of the PTP-OB protein. The preferred method consists of screening an PTP-OB-containing cDNA library constructed in a bacteriophage or plasmid shuttle vector with a partial cDNA encoding the PTP-OB protein. This partial cDNA is obtained by the specific PCR amplification of PTP-OB DNA fragments through the design of degenerate oligonucleotide primers from the amino acid sequence known for other PTP-OB-family protein tyrosine phosphatases which are related to the PTP-OB protein.

It is readily apparent to those skilled in the art that other types of libraries, as well as libraries constructed from other cells or cell types, may be useful for isolating PTP-OB-encoding DNA. Other types of libraries include, but are not limited to, cDNA libraries derived from other cells or cell lines other than human such as mouse or rat cells, and genomic DNA libraries.

It is readily apparent to those skilled in the art that suitable cDNA libraries may be prepared from cells or cell lines which have PTP-OB activity. The selection of cells or cell lines for use in preparing a cDNA library to isolate PTP-OB cDNA may be done by first measuring cell associated PTP-OB activity using the known assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding PTP-OB may also be isolated from a suitable genomic DNA library.

Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone the PTP-OB gene by one of the preferred methods, the amino acid sequence or DNA sequence of PTP-OB or a homologous protein may be necessary. To accomplish this, PTP-OB protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial PTP-OB DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the PTP-OB sequence but others in the set will be capable of hybridizing to PTP-OB DNA even in the presence of DNA oligonucleotides with mismatches. The mismatched DNA oligonucleotides may still sufficiently hybridize to the PTP-OB DNA to permit identification and isolation of PTP-OB encoding DNA.

Using one of the preferred methods, cDNA clones encoding PTP-OB are isolated in a two-stage approach employing polymerase chain reaction (PCR) based technology and cDNA library screening. In the first stage, $NH_2$-terminal and internal amino acid sequence information from the purified PTP-OB or a homologous protein is used to design degenerate oligonucleotide primers for the amplification of PTP-OB -specific DNA fragments. In the second stage, these fragments are cloned to serve as probes for the isolation of full length cDNA from a cDNA library derived from human osteosarcoma or brain cells.

The sequence for the near full-length cDNA encoding PTP-OB is shown in Seq.Id.No.:6, and was designated clone PTP-OB. The deduced amino acid sequence of PTP-OB from the cloned cDNA is shown in Seq.Id.No.:5. Inspection of the determined cDNA sequence reveals the presence of a single, large open reading frame that encodes for an approximately 1911 amino acid protein.

The cloned PTP-OB cDNA obtained through the methods described above may be recombinantly expressed by molecular cloning into an expression vector containing a suitable promoter and other appropriate transcription regulatory elements, and transferred into prokaryotic or eukaryotic host cells to produce recombinant PTP-OB. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant PTP-OB in mammalian cells. Commercially available mammalian expression vectors which may be suitable for recombinant PTP-OB expression, include but are not limited to, pMClneo (Stratagene), pXT1 (Stratagene), pSG5 (Stratagene), pcDNAI, pcDNAIamp (Invitrogen), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

DNA encoding PTP-OB may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce PTP-OB protein. Identification of PTP-OB expressing cells may be done by several means, including but not limited to immunological reactivity with anti-PTP-OB antibodies, and the presence of host cell-associated PTP-OB activity.

Expression of PTP-OB DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the PTP-OB cDNA sequence(s) that yields optimal levels of PTP-OB protein, PTP-OB cDNA molecules including but not limited to the following can be constructed: the full-length open reading frame of the PTP-OB cDNA and various constructs containing portions of the cDNA encoding only specific domains of the protein or rearranged domains of the protein. All constructs can be designed to contain none, all or portions of the 5' and/or 3' untranslated region of PTP-OB cDNA. PTP-OB activity and levels of protein expression can be determined following the introduction, both singly and in combination, of these constructs into appropriate host cells. Following determination of the PTP-OB cDNA cassette yielding optimal expression in transient assays, this PTP-OB cDNA construct is transferred to a variety of expression vectors (including recombinant viruses), including but not limited to those for mammalian cells, plant cells, insect cells, oocytes, bacteria, and yeast cells.

Levels of PTP-OB protein in host cells is quantitated by a variety of techniques including, but not limited to, immunoaffinity and/or ligand affinity techniques. PTP-OB-specific affinity beads or PTP-OB-specific antibodies are used to isolate $^{35}$S-methionine labelled or unlabelled PTP-OB protein. Labelled PTP-OB protein is analyzed by SDS-PAGE. Unlabelled PTP-OB protein is detected by Western blotting, ELISA or RIA assays employing PTP-OB specific antibodies.

Following expression of PTP-OB in a host cell, PTP-OB protein may be recovered to provide PTP-OB in active form. Several PTP-OB purification procedures are available and suitable for use. Recombinant PTP-OB may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant PTP-OB can be separated from other cellular proteins by use of an immuno-affinity column made with monoclonal or polyclonal antibodies specific for full length PTP-OB, or polypeptide fragments of PTP-OB.

Monospecific antibodies to PTP-OB are purified from mammalian antisera containing antibodies reactive against PTP-OB or are prepared as monoclonal antibodies reactive with PTP-OB using the technique of Kohler and Milstein, Nature 256: 495–497 (1975). Monospecific antibody as used herein is defined as a single antibody species or multiple antibody species with homogenous binding characteristics for PTP-OB. Homogenous binding as used herein refers to the ability of the antibody species to bind to a specific antigen or epitope, such as those associated with the PTP-OB, as described above. PTP-OB specific antibodies are raised by immunizing animals such as mice, rats, guinea pigs, rabbits, goats, horses and the like, with an appropriate concentration of PTP-OB either with or without an immune adjuvant.

Preimmune serum is collected prior to the first immunization. Each animal receives between about 0.1 μg and about 1000 μg of PTP-OB associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the PTP-OB protein in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of PTP-OB in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with PTP-OB are prepared by immunizing inbred mice, preferably Balb/c, with PTP-OB. The mice are immunized by the IP or SC route with about 1 μg to about 100 μg, preferably about 10 μg, of PTP-OB in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 μg of PTP-OB in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using PTP-OB as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-PTP-OB mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of PTP-OB in body fluids or tissue and cell extracts.

It is readily apparent to those skilled in the art that the above described methods for producing monospecific antibodies may be utilized to produce antibodies specific for PTP-OB polypeptide fragments, or full-length PTP-OB polypeptide.

PTP-OB antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing PTP-OB or PTP-OB fragments are slowly passed through the column. The column is then washed with phosphate buffered saline until the optical density ($A_{280}$) falls to background, then the protein is eluted with 0.23 M glycine-HCl (pH 2.6). The purified PTP-OB protein is then dialyzed against phosphate buffered saline.

The novel PTP-OB protein tyrosine phosphatase of the present invention is suitable for use in an assay procedure for the identification of compounds which modulate the PTP-OB activity. Modulating PTP-OB activity, as described herein includes the inhibition or activation of the protein and also includes directly or indirectly affecting the normal regulation of the PTP-OB activity. Compounds which modulate the PTP-OB activity include agonists, antagonists, inhibitors, activators, and compounds which directly or indirectly affect regulation of the PTP-OB activity.

The PTP-OB protein tyrosine phosphatase of the present invention may be obtained from both native and recombinant sources for use in an assay procedure to identify PTP-OB modulators. In general, an assay procedure to identify PTP-OB modulators will contain the PTP-OB-protein of the present invention, and a test compound or sample which contains a putative PTP-OB modulator. The test compounds or samples may be tested directly on, for example, purified PTP-OB protein whether native or recombinant, subcellular fractions of PTP-OB-producing cells whether native or recombinant, and/or whole cells expressing the PTP-OB whether native or recombinant. The test compound or sample may be added to the PTP-OB in the presence or absence of a known PTP-OB modulator. The modulating activity of the test compound or sample may be determined by, for example, analyzing the ability of the test compound or sample to bind to PTP-OB protein, activate the protein, inhibit PTP-OB activity, inhibit or enhance the binding of other compounds to the PTP-OB protein, modifying receptor regulation, or modifying an intracellular activity.

The identification of modulators of PTP-OB activity are useful in treating disease states involving the PTP-OB activity such as osteoporosis. Other compounds may be useful for stimulating or inhibiting activity of the enzyme. These compounds are useful for the prevention and treatment of bone loss and the stimulation of bone formation. Such compounds could be of use in the treatment of diseases in which activation or inactivation of the PTP-OB protein results in either cellular proliferation, cell death, nonproliferation, induction of cellular neoplastic transformations or metastatic tumor growth and hence could be used in the prevention and/or treatment of cancers such as lung cancer and osteosarcoma. The isolation and purification of an PTP-OB-encoding DNA molecule would be useful for establishing the tissue distribution of PTP-OB as well as establishing a process for identifying compounds which modulate PTP-OB activity.

Isolated and purified PTP-OB DNA would also be useful for the recombinant production of large quantities of PTP-OB protein. The ability to produce large quantities of the protein would be useful for the production of a therapeutic agent comprising PTP-OB protein. A therapeutic agent comprised of PTP-OB protein would be useful in the treatment of PTP-OB-related diseases or conditions which are PTP-OB responsive.

By molecular cloning and DNA sequencing a new member of the protein tyrosine phosphates gene family, termed PTP-OB, was identified. PTP-OB has a receptor like structure and has the characteristic cytoplasmic protein tyrosine phosphatase region. The protein is composed of 1914 amino acid residues and shares similarities to the tyrosine phosphatases LAR, PTPδ and other known LAR related PTPases. Sequence analysis revealed two highly hydrophobic regions in PTP-OB protein. One, located at the amino terminus end, is likely to be the signal peptide. The second highly hydrophobic segment that is followed by positively charged residues is likely to serve as a transmembrane domain. In the cytoplasmic region, PTP-OB contains two tandem PTPase-like domains that are found in PTPase family. Sequence comparison with the known PTPases demonstrated that PTP-OB is homologues to LAR and PTPδ (Streuli, M. et al., 1988, J.Exp.Med., 168, pp.1523–1530; Krueger, N. X. et al., 1990, EMBO J., 9, pp.3241–3252). The overall amino acid sequence homology approaches 68% and 59% respectively. Although the primary amino acid of extracellular regions diverged from that of LAR, the extracellular region of PTP-OB was observed to contain the three Ig-like domains and eight fibronectin type-III like domains that were found in LAR (Streuli, M. supra).

Northern hybridization experiments with RNA from various cell and tissues indicated that both PTP-OB and PTPδ were expressed in bone and brain derived cells or tissues. Relatively high levels of PTP-OB and PTPδ transcripts were found in RNA isolated from human osteosarcoma tumor, human giant cell tumor, rat tibia and in relatively mature cultured osteoblasts isolated from mouse calvaria. Since osteosarcoma tumor is abundant with osteoblastic cells, and giant cell tumor is a mixed cell population of multinucleated osteoclast-like cells and osteoblastic cells and other non defined cells, it is likely that in bone, the osteoblastic cells were the source of PTP-OB and PTPδ RNA. In addition to the expression in bone RNA encoding PTP-OB and PTPδ were found in human brain as well in RNA isolated from the human glioblastoma tumor cell line U340. Overall, the expression of PTP-OB was more restricted to brain or bone derived cells and tissues than that of PTPδ. In addition to the expression in brain and bone, low levels of PTPδ were found in RNA isolated from lung, liver, kidney and pancreas. Although the complete sequence of PTPδ is not known, from the available sequences, it appeared to be structurally related to LAR and to PTP-OB. Studies with the similar PTPases in drosophila, suggested that these receptor-like PTPases that share structural features with cell adhesion molecules are involved with cell to cell or cell to matrix interactions. For both brain and bone, cell to cell or cell to matrix contacts are continually modified in an ongoing process. In bone, these receptor-like PTPases, may regulate the interaction of osteoblasts with each other or with the bone matrix. Experiments with cultured osteoblats, showed that vanadate, a PTPase inhibitor, stimulated cell proliferation and the synthesis of bone collagen (Lau et al, supra). These findings, suggest that these PTPases may play an important function in osteoblasts and their exact functions are yet to be determined.

Mouse bone marrow cells are induced to differentiate into osteoclast-like cells by co-culture with neonatal calvaria osteoblasts, in the presence of $1,25(OH)_2D_3$. These cells can resorb bone and exhibit markers, such as TRAP positive staining, calcitonin receptors and vitronectin receptors, that are associated with osteoclasts. Furthermore, like primary osteoclasts, the cells contain multiple nuclei as a result of cell fusion [Takahashi, N. T., N. Akastu, Udagawa, T. Sasaki, A. Yamaguchi, J. M. Mosley, T. J. Martin, and T. Suda. 1988. Osteoblastic cells are involved in osteoclast formation. Endocrinology 123:2600–2602]. TRAP positive cells produced in the co-culture of osteoblasts and bone marrow cells can be recognized starting at four days of co-culture. The majority of the multinucleated osteoclast-like cells (70–80%) appear after six to seven days.

To identify the PTPs expressed in osteoclasts, a cDNA library prepared from the in vitro-generated mouse osteo- clasts was screened under non-stringent hybridization conditions. A cDNA fragment that codes for the amino acid residues of the cytoplasmic region of PTPα was used as probe [Kaplan, R., B. Morse, K. Huebner, C. Croce, R. Howk, M. Ravera, G. Ricca, M. Jaye, and J. Schlessinger, 1990. Cloning of three human tyrosine phosphatases reveals a multigene family of receptor-linked protein-tyrosine-phosphatases expressed in brain. Proc. Natl. Acad. Sci. USA 87:7000–7004; Sap, J., P. D'Eustachio, D. Givol, and J. Schlessinger. 1990. Cloning and expression of a widely expressed receptor tyrosine phosphatase. Proc. Natl. Acad. Sci. USA 87:6112–6116; Matthews, R. J., E. D. Cahir, and M. L. Thomas. 1990. Identification of an additional member of the protein-tyrosine-phosphatase family: evidence for alternative splicing in the tyrosine phosphatase domain. Proc. Natl. Acad. Sci. USA. 87:4444–4448; Krueger, N. X., M. Streuli, and H. Saito. 1990. Structural diversity and evolution of human receptor-like protein tyrosine phosphatases. EMBO J. 9:3241–3252]. Several positive clones were obtained, and were analyzed by restriction enzyme digestion and cDNA sequencing. It was found that in addition to the cDNA for mouse PTPα, many clones were obtained that coded for a different PTP similar to the subsequently published human hPTPε, cloned from a cDNA library of human placenta [Krueger et al., supra]. We consider this to be the cDNA of mouse PTPε (mPTPε).

Sequence analysis revealed that the mouse mPTPε is composed of 699 amino acid residues and has the structure of a transmembrane protein (FIG. 11 (SEQ.ID.NO.: 7)). A putative signal peptide is located next to the translation start site and a hydrophobic region between amino acid residues 47 to 70 is most likely a transmembrane domain. Similar to the hPTPε, the mPTPε contains a cytoplasmic region with two tandem catalytic domains and a relatively short extracellular domain of 45–47 amino acid residues. In the putative mature protein, the extracellular region would be of 25 to 27 amino acid residues with two potential N-glycosylation sites. As indicated for hPTPε, no stop codon precedes the first codon for methionine, therefore it is noteworthy that although the 5' untranslated sequences of hPTPε and mPTPε are different, the putative translation start site of mPTPε is identical to that of hPTPε. Overall, the mPTPε and the hPTPε share 93% of the amino acid residues; most of the sequence differences are concentrated in the putative extracellular regions. Compared to human PTPε, the mouse PTPε (SEQ.ID.NO.: 7) has a few amino acid substitutions, a deletion of two amino acids in the transmembrane domain and an additional amino acid residue in the short extracellular region.

Tissue distribution of PTPε expression

Hybridization of mPTPε cDNA to the mRNA isolated from enriched populations of in vitro differentiated osteoclastic cells revealed a major transcript of about 5 kb and a minor transcript of about 2 kb. Hybridization of mPTPε cDNA to mRNA isolated from rat tissues, including spleen, uterus, intestine, brain, muscle, bone (tibia), lung, ovary, liver, kidney and heart did not reveal any PTPε transcripts. In similar hybridization experiments, no PTPε transcripts in mRNA isolated from the following human tissues were detected: brain, placenta, lung, liver, skeletal muscle, kidney, and pancreas. To further test whether PTPε is expressed in osteoclasts from other species, we tested the expression of PTPε in a human giant cell tumor (osteoclastoma) and in an in vitro generated chicken osteoclast preparation, both highly enriched in multinucleated osteoclastic cells. PTPε transcripts were present in RNA from both sources. No expression of PTPε was found in osteosarcoma tumors that do not contain osteoclasts, or in RNA isolated from granulomatous tissue that is rich in other cell types.

To study the potential role of PTPε in osteoclasts, we followed the expression of PTPε during osteoclast differentiation. Total RNA was isolated from 1,25(OH)$_2$D$_3$-treated co-cultures of bone marrow and from osteoblastic mouse calvaria cells at various time points, and the expression of PTPε was assessed by Northern hybridization. We found that PTPε expression correlated with osteoclast differentiation. PTPε mRNA was first detected at four days of co-culture and increased thereafter to reach maximal expression at six days, when the number of osteoclastic cells peaked. No PTPε mRNA transcripts were detected when 1,25(OH)$_2$D$_3$ (10 nM) was omitted from the co-culture or when osteoblasts were cultured alone, with or without 1,25(OH)$_2$D$_3$. The PTPε mRNA was enriched several-fold in RNA prepared from enriched osteoclasts. These observations indicate that the RNA for PTPε originated from the osteoclasts and not from the osteoblasts.

Since PTPα has a widespread tissue distribution, and is very similar to PTPε, we tested the expression of this PTP in the co-cultured cells. Hybridization with the PTPα cDNA to the same filters showed that PTPα mRNA was constitutively expressed and did not change during the co-culture period. The PTPα RNA was present in both the cultured osteoblasts and the co-cultured cells and was not dependent on the presence of 1,25(OH)$_2$D$_3$. The level of PTPα transcripts was lower in RNA isolated from the enriched osteoclasts, which could be due to osteoblast contamination or lower levels of PTPα in osteoclastic cells.

The following examples are provided as illustrative of the present invention without, however, limiting the same thereto.

EXAMPLE 1

Primer Design

Degenerate DNA primers were designed to recognize the coding region of the conserved amino acid residues of a typical protein tyrosine phosphatase domain. The sense primer, PH4, was the degenerate oligomer, 5' CTTCTAGAA (A/G)TG(T/C)GC(G/T/C/A)CA(A/G)TA(T/C)TGGCC (SEQ.ID.NO.: 1), that was prepared according to the conserved amino acid residues Lys Cys Ala Gln Tyr Trp Pro (SEQ.ID.NO.: 2). The antisense primer, PH2a, 5'. GAAGCTTCC(C/A)A(C/T)(G/C/T/A/)CCTGCAC(T/A) (A/G)CA(G/A) TG(C/G/T/A)AC (SEQ.ID.NO.: 3), was designed to complement the DNA sequences coding for the amino acid residues Val His Cys Ser Ala Gly Val Gly (SEQ.ID.NO.: 4) of the tyrosine phosphatase domain.

cDNA Amplification

Single stranded randomly primed cDNA was prepared with the Mo-MLV reverse transcriptase (BRL) from RNA isolated from a human osteosarcoma Saos-2/B10 cells. The cDNA reaction (25 μl) was diluted into 300 μl water and heat denatured at 95° C. for 5 minutes and quickly chilled on ice. The cDNA (5 μl) and the above primer pair, PH2a and PH4 (0.5 μM each) were employed in the amplification reaction with the Amplitaq kit and the DNA thermal cycler (Perkin Elmer, Cetus). The amplification cycles were as follows: denaturation at 94° C., 70 seconds; annealing at 50°C. for 135 seconds; 3 minutes of gradual increase of the temperature to 72°C.; extension at 72°C., 4 minutes for 40 cycles. The amplified fragments were separated by electrophoresis on 5% polyacrylamide gel, cloned into plasmids and sequenced. The cDNA clones were than used to screen lamda gt11 cDNA libraries and positive clones were isolated and their two DNA strands were sequenced.

Screening of cDNA Libraries

The cDNA libraries of human fetal lungs that were prepared from a mixture of 19-week and 21-week-old fetuses and the human fetal brain of a 26-week-old male fetus were purchased (Clontech, CA). The human giant cell tumor and the human U340 brain tumor cell cDNA libraries were constructed in lamda gt11 by using a mixture of oligo dT and random primers (Super Script Choice System, BRL, MD). The cDNA libraries were plated at a density of 30,000 plaques per 150-mm plate and transferred to nylon filters (Hybond N, Amersham). A half or one million of recombinants of each library were screened using 32P-labeled probe. Positive plaques were identified and selected clones were inserted into plasmids and sequenced.

Cloning of PTP-OB cDNA

The polymerase chain reaction (PCR) strategy was employed in order to identify the PTPases that are expressed in bone-derived cells. Total RNA was isolated from human osteosarcoma SAOS-2/B10 cells after six of hours treatment with TPA or a control solution. The cDNA was prepared and subjected to PCR amplification with DNA primers that were synthesized according to the conserved amino acid residues of the tyrosine phosphatase domain found in the members of the PTP family. After separation of the amplification products on 5% polyacrylamide gel, multiple DNA fragments, with the size range of 290–315 bp, were observed with the reaction that contained the cDNA of the TPA treated cells. No detectable hybridizing DNA fragments were observed when the cDNA from the control cells was used as template. The DNA fragments were cloned into plasmid vectors and sequenced in their entirety. After sequence analysis, we found that the various cDNA clones represented DNA fragments of five different PTPases. Four of these PTPases were the known PTPδ (Krueger et al, 1990 EMBO J 9:3241–3252), PTPgamma (Sap et al, 1990, Proc.Natl.Acad.Sci. USA, 87, pp.6112–6116; Kaplan et al., 1990. Proc.Natl.Acad.Sci. USA 87:700–7004), PTPalpha (Matthews et al., 1990, Proc.Natl.Acad.Sci. USA; 89, pp.2980–2984; Kaplan et al., supra), and PTP MEG (Gu, M. et al., 1992, Proc.Natl.Acad.Sci. USA, 89, pp.2980–2984). The fifth clone, named PTP-OB, is a novel, yet unreported, PTPase gene product.

To obtain a complete cDNA sequence for the human PTP-OB, several cDNA libraries were screened which were either purchased or prepared according to standard methods. From a human fetal lung library, three cDNA clones were obtained that hybridized with the amplified 283 bp DNA fragment of PTP-OB. Analysis of the DNA sequence revealed that these three clones were identical and their sequences matched that of PTP-OB. Complete DNA sequencing of clone PTP-OB-17, revealed a 1714 bp cDNA that contained an open reading frame coding for a PTP like protein that was interrupted by a putative termination codon (FIG. 1).

To find additional cDNA sequences, we screened the cDNA library of the giant cell tumor with the cDNA of PTP-OB-17. Seven cDNA clones were identified and the longest cDNA, PTP-OB-10, was analyzed. Sequence analysis revealed a 3613 bp open reading frame that encodes for 1204 amino acid residues (FIG. 1). Since the expression of PTP-OB was found in brain tissue a human brain cDNA library was screened with the 350 bp DNA fragment that corresponded to the most 5' end of clone PTP-OB-10. Sixty positive clones were identified and after size selection and partial sequencing of several lambda clones, a clone of 3588 bp was identified, PTP-OB-133, that contained an open reading frame that starts with the putative initiation codon at the 5' end. Overall, analysis of the assembled cDNA sequences revealed a cDNA of 5988 nucleotides that contained a long open reading frame of 5733 bp that codes for 1911 amino acid residues. At the 5' end of the cDNA three initiation codons were identified. The first methionine codon is the most suitable translation start site. A comparison of PTP-OB protein the known PTPases showed that it is most similar to PTPases LAR and LAR related PTPases. The amino acid sequence of PTP-OB showed 68% identity with LAR and 59% with PTPδ. Similar to LAR, PTP-OB has a receptor-like structure. A highly hydrophobic region is located next to the putative initiation codon, and is probably the signal peptide. According to the consensus rules for signal peptide cleavage, the thirtieth amino acid residue is probably the first amino acid of the mature protein. A second highly hydrophobic domain is found between amino acid residues 1253 to 1277 and is most likely to function as the transmembrane domain. Similar to observations for LAR, analysis of the primary amino acid sequence of the putative extracellular region indicated three repeats of immunoglobulin-like domains and eight fibronectin type III-like repeats (Streuli et a 1998). According to the consensus glycosylation sites, three potential N-linked glycosylation sites at position 250, 721 and 919 were identified. The extracellular domain of PTP-OB is 58% identical to the parallel domain of LAR and 40% identical to DLAR and is closely related to other LAR related PTPase proteins.

The cytoplasmic domain of PTP-OB is composed of 626 amino acid residues. In this region the two tandem repeats of protein tyrosine phosphatase domains are recognized. The cytoplasmic region is highly conserved and it is 95% and 87% identical to the parallel domains of LAR and PTPδ respectively.

Comparing the overlapping sequences of PTP-OB-10 and PTP-OB-133 revealed that the clone isolated from the brain library contained a deletion of 1225 nucleotides, between 1828–3055 of the complete sequence, that maintained the open reading frame. Partial analysis of several other clones obtained from the brain library, revealed that they all had similar deletions thus coding for a protein with an extracellular domain that is shorter by 409 amino acid residues (between residues 604–1013) and with a substitution of a valine residue, V1014, to an isoleucine residue, i1014.

EXAMPLE 2

Tissue Distribution of PTP-OB Expression

RNA Hybridization

RNA was isolated by the modified guanidinium hydrochloride method or by guanidinium isothiocyanate method. Total RNA (20–30 μg) and polyA selected RNA (2–5 μg) were separated on formaldehyde agarose gels and transferred nylon filters and subjected to hybridization with (Hybond N, Amersham). A Northern blot of polyA+ RNA of various human tissues was purchased from Clontech, CA. The hybridization solutions contained 40–50% formamide (Hybrisol I and II, Oncor). After hybridization, the filters were washed in a solution of 2×SSC containing 0.1% SDS, and finally in 0.2×SSC/0.1% SDS solution at 55°C., and exposed to X-ray film (XAR-2, Kodak) with intensifying screen at −70°C. for up to 10 days.

Preparation of RNA and Hybridization.

Rat tibiae were dissected free of soft tissue and the bone marrow was removed from the bones. RNA was isolated from these bones by the modified guanidinium hydrochloride method [Nemeth, G. G., A. Heydemann, and M. E. Bolander. 1989. Isolation and analysis of ribonucleic acids from skeletal tissues. Anal. Biochem. 183:301–304] and the guanidinium isothiocyanate method [Kaplan, R., B. Morse, K. Huebner, C. Croce, R. Howk, M. Ravera, G. Ricca, M. Jaye, and J. Schlessinger. 1990. Cloning of three human tyrosine phosphatases reveals a multigene family of receptor-linked protein-tyrosine-phosphatases expressed in brain. Proc. Natl. Acad. Sci. USA 87:7000–7004]. Total RNA (20–30 μg) or polyA+ selected RNA (2–5 μg) were electrophoresed on formaldehyde-containing agarose gels and transferred to nylon filters (Hybond N, Amersham). A poly A+ RNA blot of various human tissues was purchased from Clontech, CA. Poly A+ RNA from cultured chicken osteoclasts was also prepared. The hybridization solutions contained 40–50% formamide (Hybrisol I and II, Oncor, MD). After hybridization, the filters were washed in a solution of 2×SSC/0.1% SDS, and finally in 0.2×SSC/0.1% SDS solution at 55° C., and exposed to X-ray film (XAR-2, Kodak) with an intensifying screen at −70° C.

Expression of PTP-OB mRNA

Figure 2:
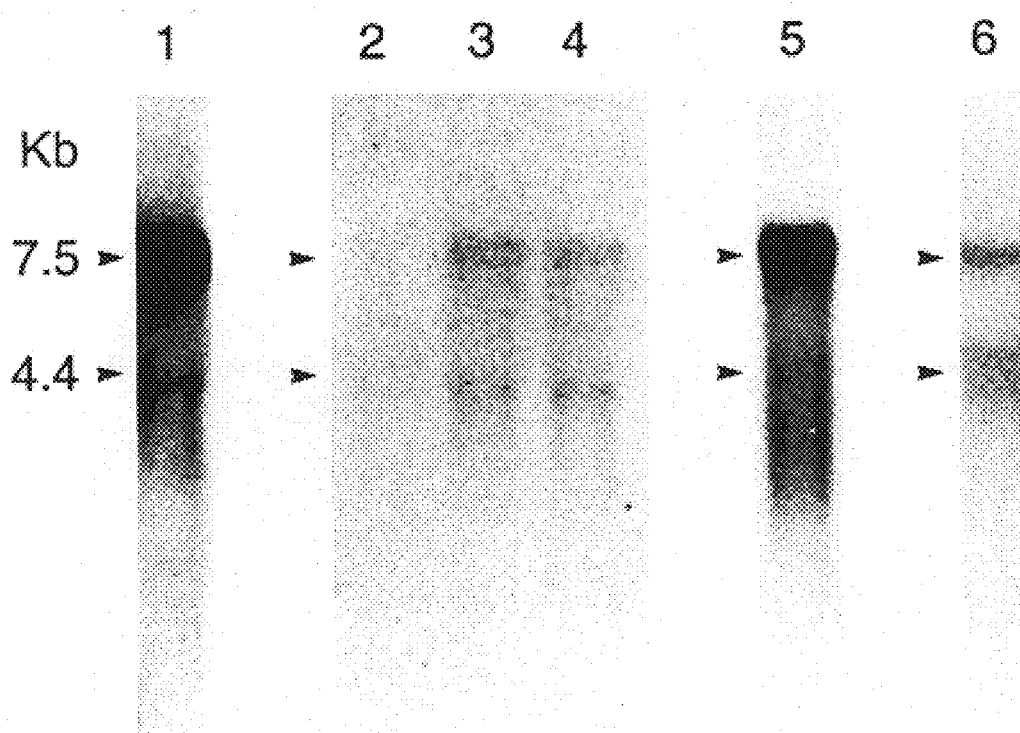
FIG. 2. Northern blots of RNA from human osteosarcoma (lane 1), human giant cell tumors (lanes 2–5), and rat tibia (lane 6) cells is shown.
Figure 3:
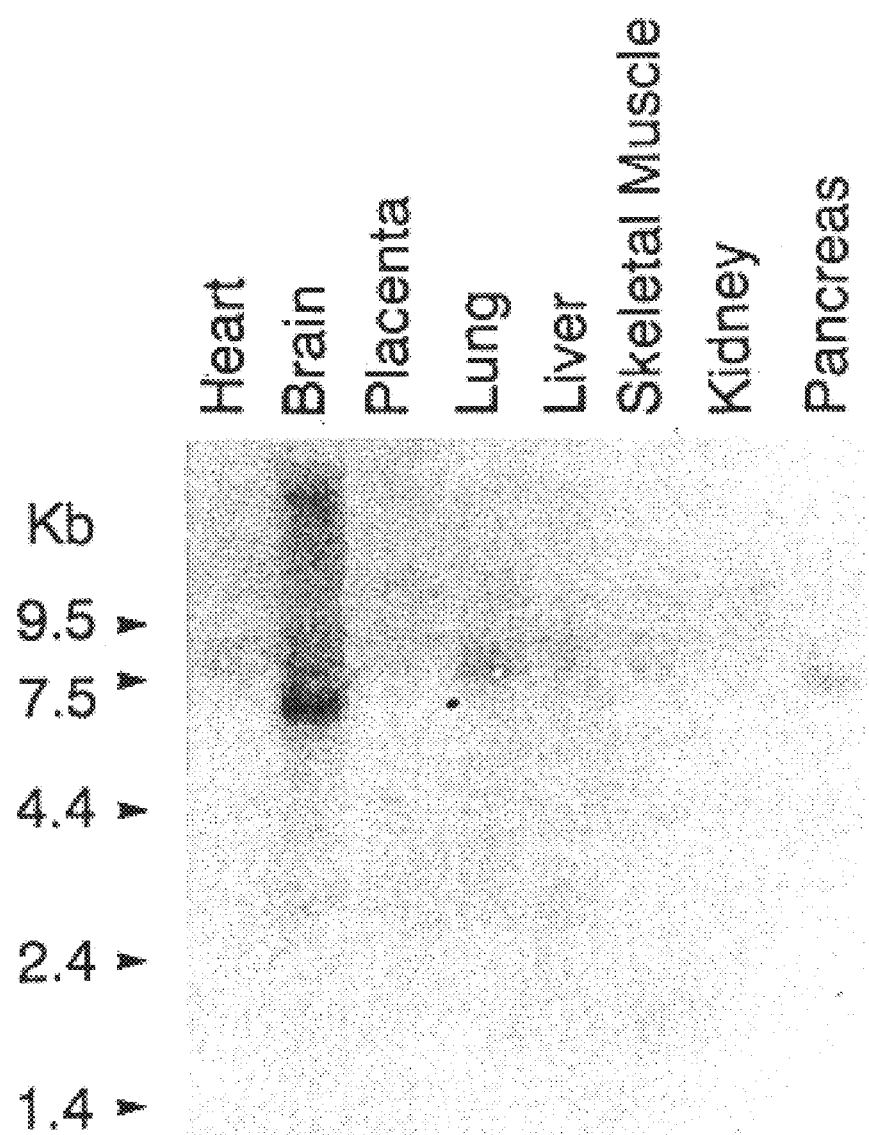
FIG. 3. A Northern blot of RNA from human tissues is shown.

PTP-OB cDNA was hybridized to RNA isolated from various cells and tissues. Northern hybridization experiments revealed that mRNA for PTP-OB is approximately 7.3 Kb. High steady state levels of PTP-OB RNA were found in human osteosarcoma tumor, giant cell tumor (GCT), and in mRNA prepared from human brain (FIGS. 2 and 3). In rat tissues, high level of expression of PTP-OB RNA was found in RNA prepared from tibia. Very low expression levels were detected in RNA isolated form lungs of one week old rat.

Figure 4:
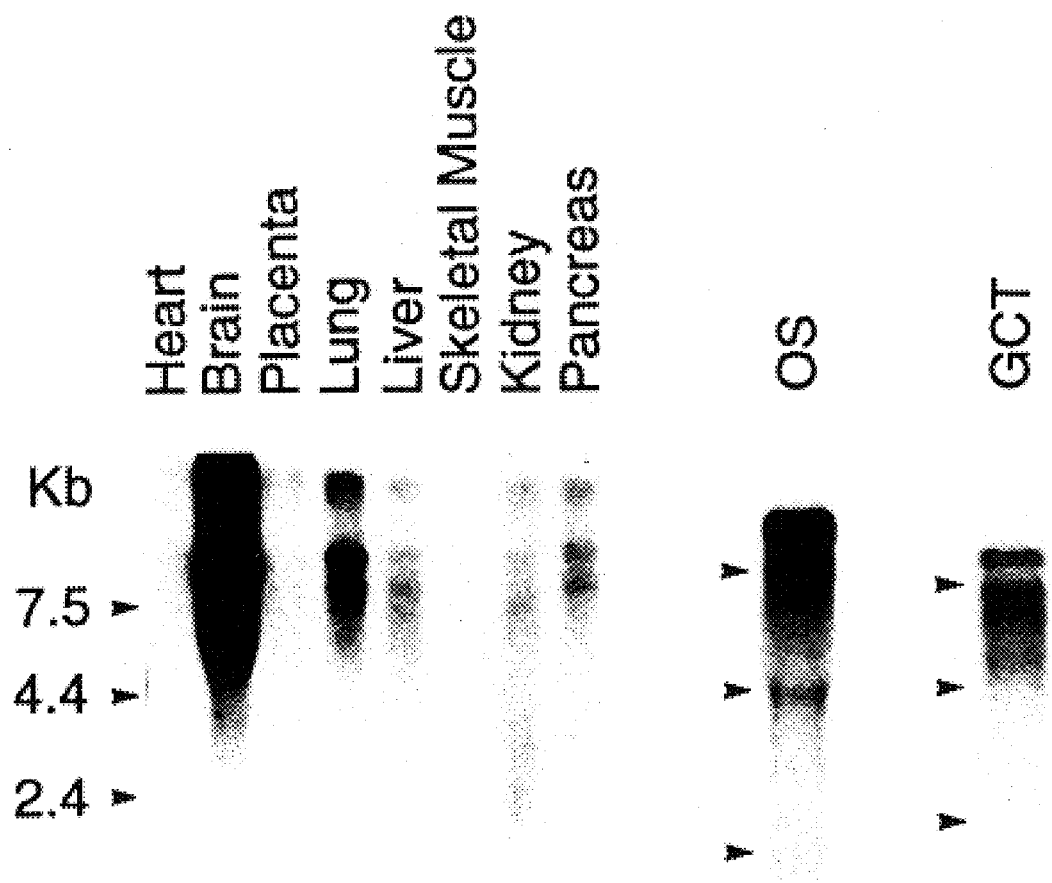
FIG. 4. Northern blots of RNA from human tissues is shown on the left, and of RNA from human tumor tissue on the right two lanes: osteosarcoma (OS) and giant cell tumor (GCT).

Hybridization experiments with the cDNA for PTPδ, showed tissue distribution that was comparable to PTP-OB. PTPδ was found to be highly expressed in brain. Lower levels of PTPδ transcripts were found in RNA isolated from lung and very low but detectable levels were observed in liver, kidney and pancreas. In bone derived cells, high expression levels of PTPδ was found in the human osteosarcoma tumor, and human giant cell tumor (FIG. 4). In cultured cells, there were high expression levels of both PTP-OB and PTPδ in osteoblasts isolated from mouse calvaria and in the human glioblastoma brain tumor U340.

EXAMPLE 3

Cloning of the PTP-OB cDNA into E. coli Expression Vectors

Recombinant PTP-OB is produced in E. coli following the transfer of the PTP-OB encoding DNA into E. coli expression vectors, including but not limited to, the pET series (Novagen). The pET vectors place PTP-OB expression under control of the tightly regulated bacteriophage T7 promoter. Following transfer of this construct into an E. coli host which contains a chromosomal copy of the T7 RNA polymerase gene driven by the inducible lac promoter, expression of PTP-OB is induced when an appropriate lac substrate (IPTG) is added to the culture. The levels of expressed PTP-OB are determined by the assays described above.

The cDNA encoding the entire open reading frame for PTP-OB is inserted into the NdeI site of pET 11a. Constructs in the positive orientation are identified by sequence analysis and used to transform the expression host strain BL21. Transformants are then used to inoculate cultures for the production of PTP-OB protein. Cultures may be grown in M9 or ZB media, whose formulation is known to those skilled in the art. After growth to an approximate $OD_{600}$= 1.5, expression of PTP-OB is induced with 1 mM IPTG for 3 hours at 37° C. Authentic PTP-OB may be found in the insoluble inclusion body fraction from these cells. Soluble PTP-OB is extracted from the inclusion body fraction with 5 M guanidine-HCl in a buffer containing 50 mM Tris-HCl (pH 8) and 100 mM dithiothreitol. Active PTP-OB is generated from this extract following dialysis against 100 volumes of 25 mM HEPES (pH 7.5), 5 mM dithiothreitol, 10% sucrose.

PTP assays

The cDNA coding for the cytoplasmic region (amino acid residues 69–699) of PTPε and PTP-OB were individually inserted in frame into the bacterial expression vector pGEX-2TX (Pharmacia), thus forming a glutathione S-transferase (GST) PTPε fusion protein and a GST-PTP-OB fusion protein. The GST-PTP-OB and GST-PTPε fusion proteins were isolated from the bacteria according to the Pharmacia protocol. The enzymatic assays were performed at optimal reaction conditions (50 mM MES, 0.15 M NaCl, 10% glycerol, pH of 5.65) at ambient temperature. As a substrate fluorescine diphosphate (FDP, Molecular Probes, Inc., Eugene, Oreg.) at the Km was used. The reaction was continuously monitored by measuring the dephosphorylated product using a Millipore Cytoflour II plate reader with an excitation wavelength of 485 nm (20 nm band width) and an emission wavelength of 530 nm (30 nm band width). The recombinant PTP-OB enzyme, purified according to the directions provided by the plasmid pGEX-2TX manufacturer, was used in the assays described herein, such as in Example 10 and 11.

EXAMPLE 4

In Vitro Translation of PTP-OB mRNA and Xenopus Oocyte Expression

PTP-OB cDNA constructs are ligated into in vitro transcription vectors (the pGEM series, Promega) for the production of synthetic mRNAs.

Synthetic mRNA is produced in sufficient quantity in vitro by cloning double stranded DNA encoding PTP-OB mRNA into a plasmid vector containing a bacteriophage promoter, linearizing the plasmid vector containing the cloned PTP-OB-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded PTP-OB-encoding DNA is cloned into the bacteriophage promoter containing vector in the proper orientation using one or more of the available restriction endonuclease cloning sites on the vector which are convenient and appropriate for cloning PTP-OB DNA. The vector with the ligated PTP-OB DNA is used to transform bacteria, and clonal isolates are analyzed for the presence of the vector with the PTP-OB DNA in the proper orientation.

Once a vector containing the PTP-OB-encoding DNA in the proper orientation is identified and isolated, it is linearized by cleavage with a restriction endonuclease at a site downstream from, and without disrupting, the PTP-OB transcription unit. The linearized plasmid is isolated and purified, and used as a template for in vitro transcription of PTP-OB mRNA.

The template DNA is then mixed with bacteriophage-specific DNA-dependent RNA polymerase in a reaction mixture which allows transcription of the DNA template forming PTP-OB mRNA. Several bacteriophage-specific DNA-dependent RNA polymerases are available, including but not limited to T3, T7, and SP6 RNA polymerase. The synthetic PTP-OB mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5' terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified PTP-OB mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic PTP-OB mRNA to produce PTP-OB protein. The microinjected oocytes are incubated to allow translation of the PTP-OB mRNA, forming PTP-OB protein.

These synthetic mRNAs are injected into Xenopus oocytes (stage 5–6) by standard procedures [Gurdon, J. B. and Wickens, M. D. Methods in Enzymol. 101: 370–386, (1983)]. Oocytes are harvested and analyzed for PTP-OB expression.

EXAMPLE 6

Cloning of PTP-OB cDNA into a Mammalian Expression Vector

PTP-OB cDNA expression cassettes are ligated at appropriate restriction endonuclease sites to the following vectors containing strong, universal mammalian promoters: pBC12BI [Cullen, B. R. Methods in Enzymol. 152: 684–704 1988], and pEE12 (CellTech EP O 338,841) and its derivatives pSZ9016-1 and p9019. p9019 represents the construction of a mammalian expression vector containing the hCM-VIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978-120 and 139778-121 using pD5 (Berker and Sharp, Nucl. Acid Res. 13: 841–857 [1985]) as template. The resulting 0.25 Kb PCR product is digested with ClaI and SpeI and ligated into the 6.7 Kb fragment of pEE 12 which had been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5′ side while Hind m and Xba I sites are appended on the 3′ side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the PTP-OB cDNA in the positive orientation with respect to the promoter are ligated into appropriate restriction sites 3′ of the promoter and identified by restriction site mapping and/or sequencing. These cDNA expression vectors are introduced into various host cells including, but not limited to: [COS-7 (ATCC# CRL1651), CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture extracts can be harvested and analyzed for PTP-OB expression as described below.

All of the vectors used for mammalian transient expression can be used to establish stable cell lines expressing PTP-OB. Unaltered PTP-OB cDNA constructs cloned into expression vectors will be expected to program host cells to make intracellular PTP-OB protein. The transfection host cells include, but are not limited to, CV-1-P [Sackevitz et al., Science 238: 1575 (1987)], tk-L [Wigler, et al. Cell 11: 223 (1977)], NS/O, and dHFr-CHO [Kaufman and Sharp, J. Mol. Biol. 159: 601, (1982)].

Co-transfection of any vector containing PTP-OB cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz. L. and Davies, J., GENE 25: 179 (1983)]; APRT, xanthine-guanine phosphoribosyl-transferase, pMAM (Clontech) [Murray, et al., Gene 31: 233 (1984)] will allow for the selection of stably transfected clones. Levels of PTP-OB are quantitated by the assays described above.

PTP-OB cDNA constructs are ligated into vectors containing amplifiable drug-resistance markers for the production of mammalian cell clones synthesizing the highest possible levels of PTP-OB. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR- CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 7

Cloning of PTP-OB cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing PTP-OB cDNA is produced by the following standard methods (In Vitrogen Maxbac Manual): the PTP-OB cDNA constructs are ligated downstream of the polyhedrin promoter in a variety of baculovirus transfer vectors, including the pAC360 and the BlueBac vector (In Vitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of β-galactosidase expression (Vialard, et al. 1990, J. Virol., 64, pp 37–50). Following plaque purification and infection of sf9 cells with PTP-OB recombinant baculovirus, PTP-OB expression is measured by the assays described above.

The cDNA encoding the entire open reading frame for PTP-OB is inserted into the BamHI site of pBlueBacII. Constructs in the positive orientation with respect to the polyhedrin promoter are identified by sequence analysis and used to transfect Sf9 cells in the presence of linear AcNPV mild type DNA.

EXAMPLE 8

Cloning of PTP-OB cDNA into a Yeast Expression Vector

Recombinant PTP-OB is produced in the yeast S. cerevisiae following the insertion of the optimal PTP-OB cDNA construct into expression vectors designed to direct the intracellular expression of heterologous proteins. For intracellular expression, vectors such as EmBLyex4 or the like are ligated to the PTP-OB cistron [Rinas, U. et al., Biotechnology 8: 543–545 (1990); Horowitz B. et al., J. Biol. Chem. 265: 4189–4192 (1989)]. The levels of expressed PTP-OB are determined by the assays described above.

EXAMPLE 9

Purification of Recombinant PTP-OB

Recombinantly produced PTP-OB may be purified by antibody affinity chromatography.

PTP-OB antibody affinity columns are made by adding the anti-PTP-OB antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents, if necessary such as detergents, and the cell culture supernatants or cell extracts containing PTP-OB or PTP-OB fragments are slowly passed through the column. The column is then washed with phosphate-buffered saline together with detergents, if necessary until the optical density (A280) falls to background, then the protein is eluted with 0.23 M glycine-HCl (pH 2.6) together with detergents, if necessary. The purified PTP-OB protein is then dialyzed against phosphate buffered saline.

EXAMPLE 10

Screening Assay to Identify Modulators of PTP Activity

Mouse osteoclasts were generated in vitro by culturing together bone marrow cells and calvariae osteoblasts. Osteoblastic cells were isolated from mouse calvariae and cultured for 24 hours. Then, freshly isolated bone marrow cells were added to the cultured osteoblasts and treated with 10 nM 1,25(OH)2D3 (D3) for seven days. Under these conditions the bone marrow cells differentiated into multinucleated osteoclast-like cells that were positively stained for tartarat resistant alkaline phosphatase (TRAP), have other osteoclast specific markers (Takahashi, N. T. et al., 1988, Endocrinol., 123, pp.2600–2602), and have the ability to resorb bone in culture. The D3 and the various inhibitors were added to the cells with fresh medium at days two and four of co-culturing. TRAP positive cells were counted in quadruplicate wells for each test condition.

Mouse bone marrow cells, were induced to differentiate into osteoclast-like cells by co-culturing with neonatal calvariae osteoblasts in a D3 dependent process. These cells were stained by tartarat resistant acid phosphatase and exhibited markers that were associated with osteoclasts, such as calcitonin receptors, and vitronectin receptors. Furthermore, like osteoclasts, the cells contained multiple nuclei as a result of cell fusion activities ( Takahashi, N. T. et al., supra). The multinucleated TRAP positive cells could be recognized as early as four days of co-culturing, but the majority of the multinucleated osteoclast-like cells (70–80%) were generated after six and seven days of co-culturing. The process was completely dependent on the treatment with vitamin D3, and no osteoclasts were formed in the absence of either D3, osteoblasts or bone marrow cells ( Takahashi, N. T. et al., supra ).

Figure 5A:
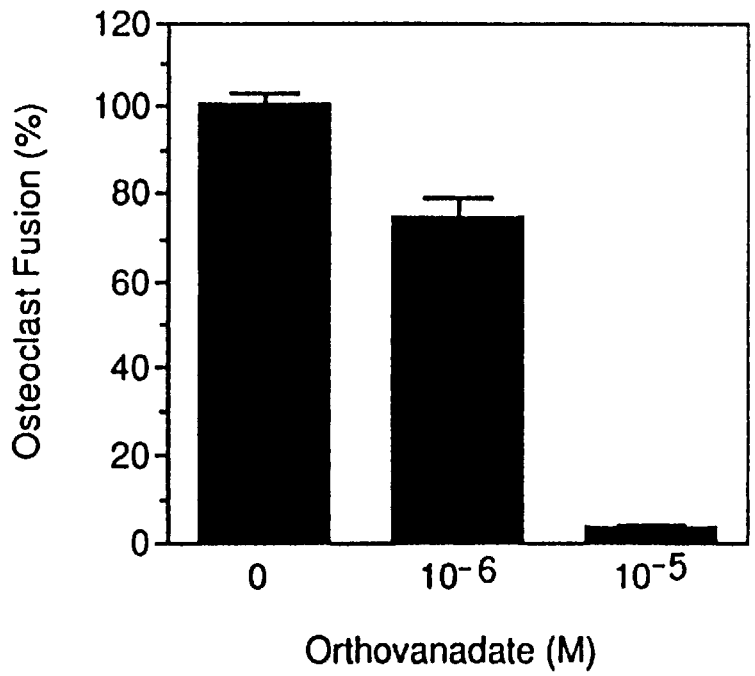
FIGS. 5A, 5B, and 5C. The effect of protein tyrosine phosphatases and protein tyrosine kinase in in vitro osteoclast formation is shown.
Figure 5B:
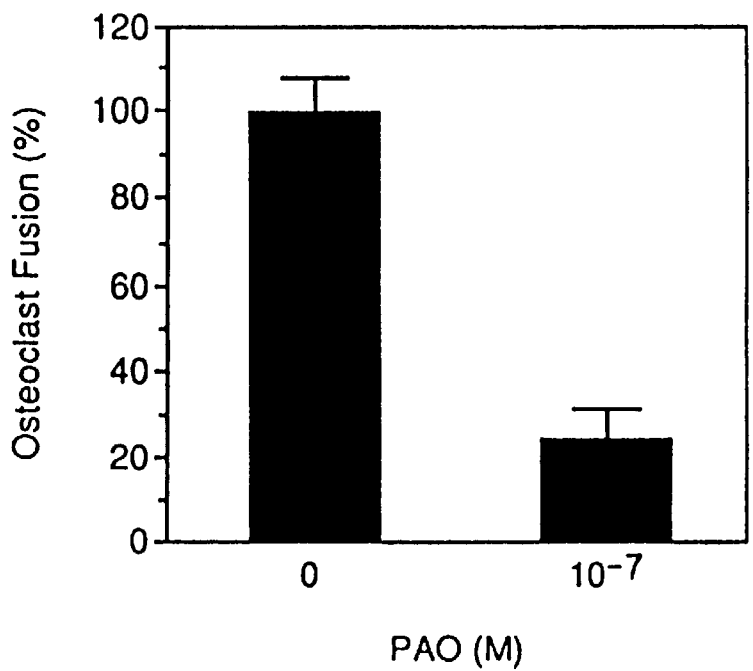
Figure 5C:
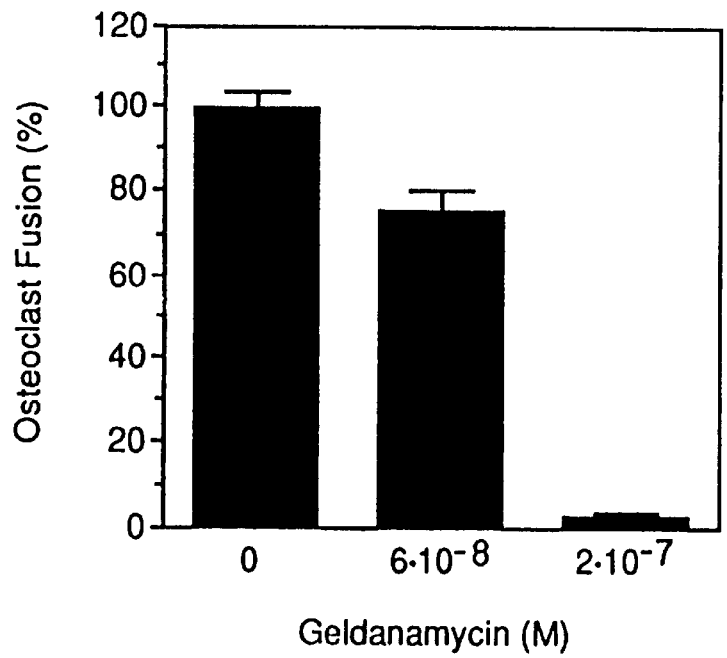

To test for the importance of PTPase activity in the generation of osteoclasts, we studied the influence of PTPase inhibitors on the differentiation of bone marrow cells in osteoclast. In these experiments, addition of orthovanadate to the co-cultured cells completely inhibited the formation of the multinucleated TRAP positive cells, with an IC 50 of 2 $\mu$M (FIG. 5). Similarly, treatment with phenylarsine oxide (PAO) strongly inhibited the formation of the multinucleated TRAP positive cells with an IC 50 of 0.2 $\mu$M (FIG. 5). Treatment with orthovanadate (10 $\mu$M) or phenylarsine oxide (0.21 $\mu$M), which markedly inhibited the formation of the fused TRAP positive cells, produced mononucleated TRAP positive cells. Thus, the major influence of the inhibitors appeared to be on the process of cell fusion. Moreover, at these concentration of PTPase inhibitors, no ill effects were observed on the co-cultured osteoblasts. To further characterize the importance of the PTPases on osteoclast formation, orthovanadate was added at different days of co-culturing and the formation of fused TRAP positive cells was measured.

Figure 6:
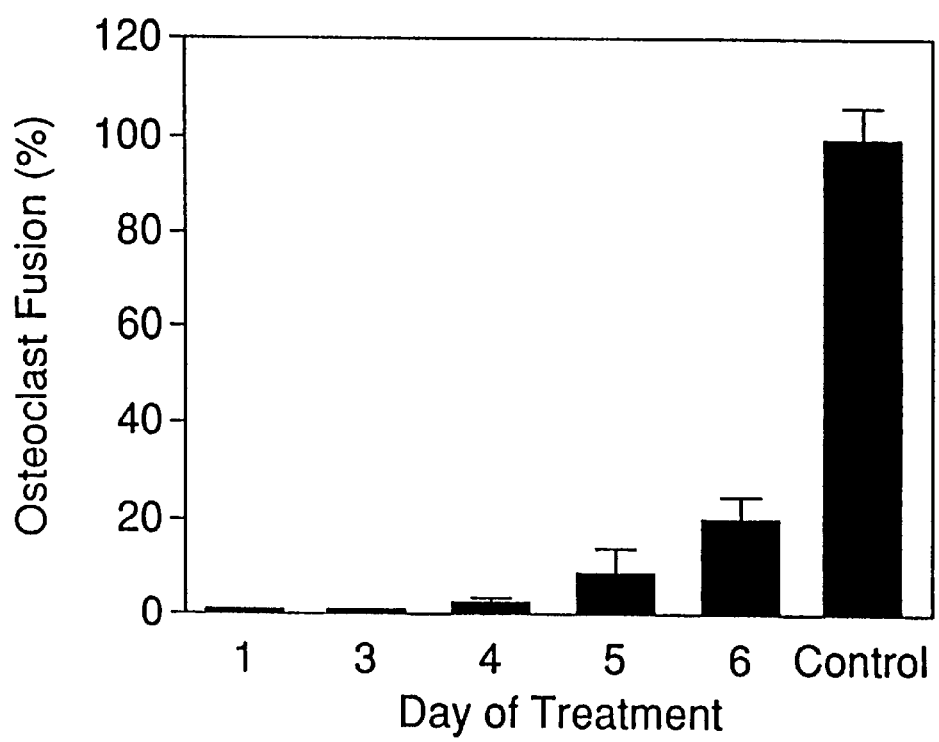
FIG. 6. The time dependent effect of orthovanadate on osteoclast cell fusion is shown.

In these experiments the orthovanadate was able to block 80% of the formation of the multinucleated TRAP positive cells when added at six days of co-culturing (FIG. 6). Addition of the PTPase inhibitor at earlier days of the co-culturing before the major cell fusion occurred had a small additional effect. To further study the role of tryosine phosphorylation in osteoclast formation, influence of geldanamycin, a tyrosine kinase inhibitor, on the formation of osteoclasts was tested. In these experiments, geldanamycin was a potent inhibitor of osteoclasts formation, with an IC 50 of 50 ng/ml (FIG. 5). Though, in contrast to the PTPase inhibitors, it completely blocked the appearance of mononuclear TRAP positive cells.

Figure 7A:
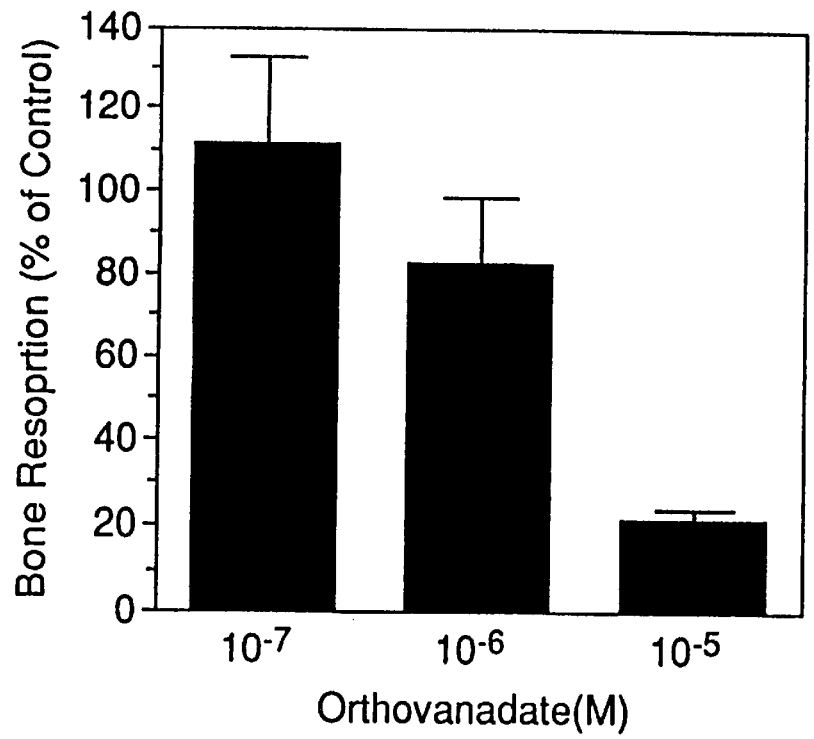
FIGS. 7A and 7B. The effect of inhibitors of protein tyrosine phosphatases and protein tyrosine kinase on in vitro bone resorption is shown.
Figure 7B:
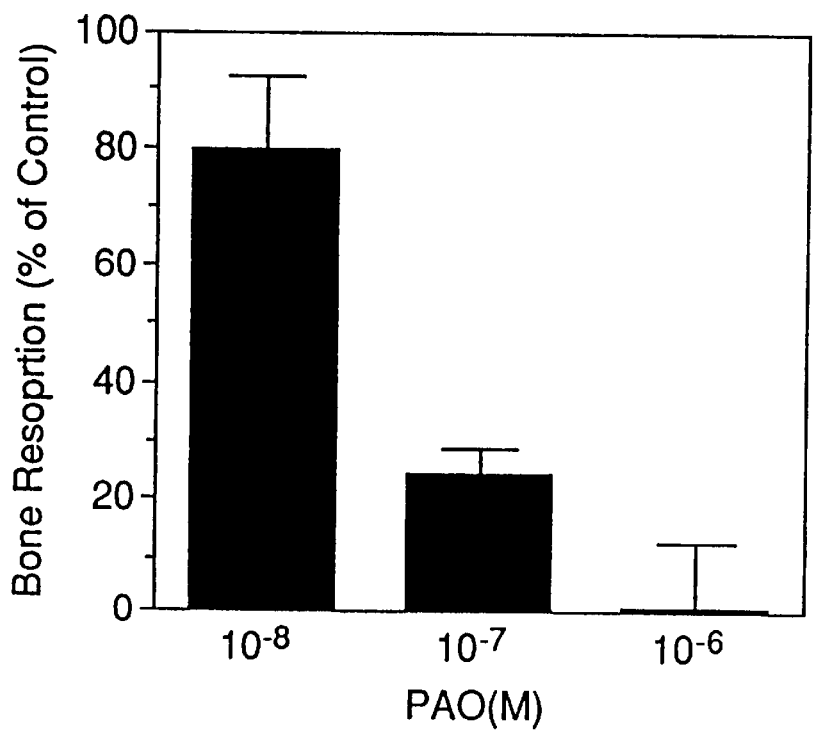

To test whether PTPase activity could influence the osteoclasts activity, the influence of the PTPase inhibitors was tested in an in vitro bone resorption assay. In these assays, freshly isolated rat osteoclasts were placed on bone slices for 24 hours and the influence of PTPase inhibitors on the number of resorbing pits in the bone slice were observed. Both orthovanadate and phenylarsine oxide were found to be potent inhibitors of bone resorption (FIG. 7), with an IC50 of 2 $\mu$M for orthovanadate and IC 50 of 0.05 $\mu$M for penylarsine oxide.

Bone Resorption Assay

Six long bones were isolated from neonatal rats and were placed in 4.5 ml 199 medium supplemented with 10% fetal bovine serum. The bones were dissected longitudinally and cells were separated by scraping. The cell suspension was filtered through a nylon mesh. Circular slices of steer bone (4.4×0.2 mm) were sonicated, sterilized and then hydrated in culture medium. The isolated cells (0.1 ml) were placed on the bone slices in 96 well tissue culture plates and incubated at 37° C., 5% $CO_2$ with a PTP inhibitor or vehicle for 24 hours. At the end of the experiment, the bone slices were sonicated, fixed with ethanol and stained with methylene blue. The resorption pits were visualized by reflection light microscopy and their number was determined [Murrills, R. J., L. S. Stein, C. P. Fey, and D. W. Dempster. 1990. The effects of parathyroid hormone (PTH) and PTH-related peptide on osteoclast resorption of bone slices in vitro: an analysis of pit size and the resorption focus. Endocrinology 127:2648–2653].

Alendronate inhibition of PTP activity

Figure 8A:
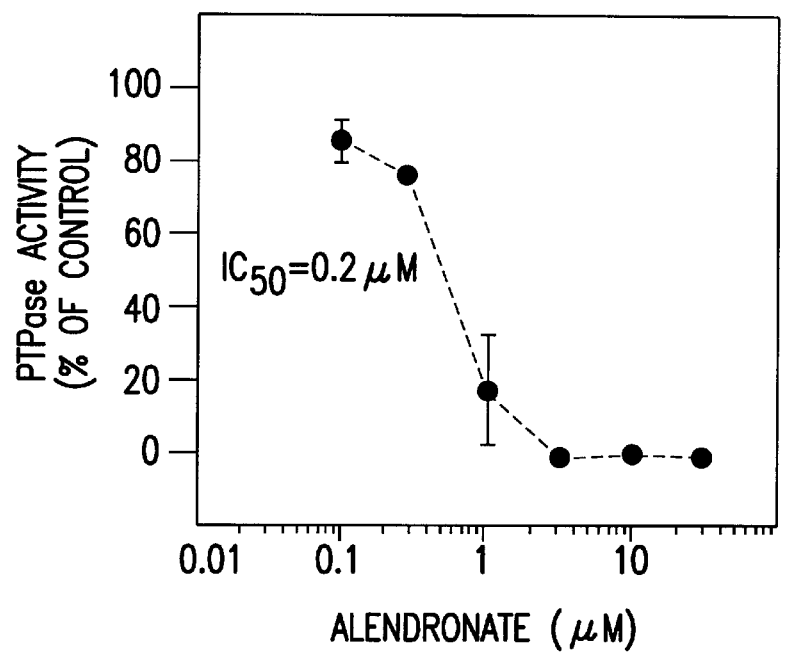
FIGS. 8A and 8B. The enzymatic activity of recombinant PTP-OB is shown in the presence and absence of inhibitors.
Figure 8B:
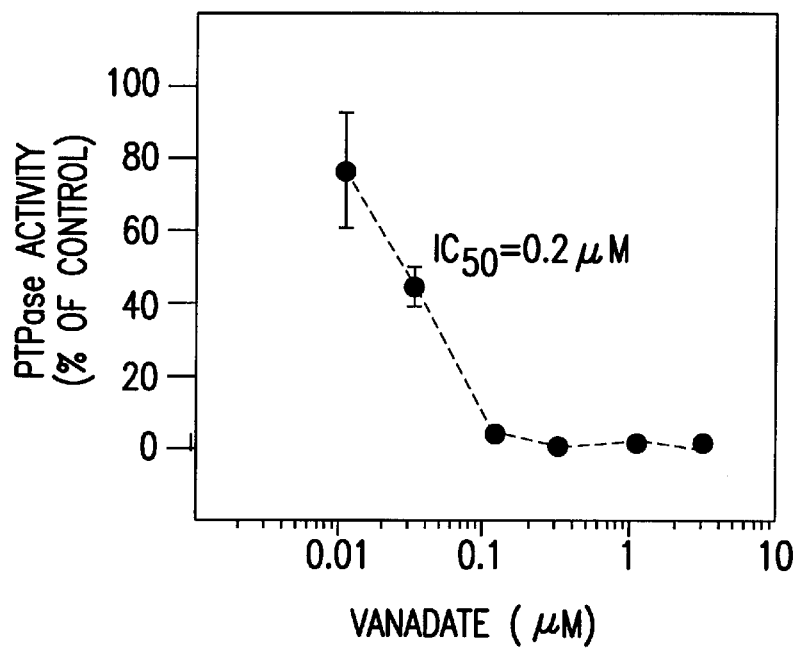

To study the enzymatic activity of PTP-OB and PTPε, we expressed the cytoplasmic domain of PTP-OB and PTPε in bacteria as a GST-fusion protein. After purification, the GST-PTP-OB and GST-PTPε fusion proteins were tested for PTP enzymatic activity and for their sensitivity to ALN and the PTP inhibitors, orthovanadate, BP, and PAO [Gordon, J. A. 1991. Use of vanadate as protein-phosphotyrosine phosphatase inhibitor. Methods Enzymol. 201:477–482; Walton, K. M., and J. E. Dixon. 1993. Protein tyrosine phosphatases. Annu. Rev. Biochem. 62:101–120] (FIG. 8). As a substrate we used FDP, previously described as a good substrate for other PTPases (34,35). PTPε effectively dephosphorylated FDP with a Km=70 $\mu$M, which is comparable to the Km values obtained for other PTPs, such as CD45, PTPδ and PTP1B. As reported with other phosphatases, the enzymatic activity of PTP-OB was sensitive to orthovanadate ($IC_{50}$ of about 0.02 uM).

BPs are organic phosphate analogues that inhibit enzymatic activities of PTP that were expressed in osteoclasts. Therefore, we tested the influence of alendronate, a potent inhibitor of bone resorption, on the enzymatic activity of PTP-OB. In these studies, we determined that alendronate is also a potent inhibitor of PTP-OB with an $IC_{50}$ of 0.2 $\mu$M. Etidronate, another bisphosphonate, also inhibited PTPε activity with an $IC_{50}$ of about 0.4 uM. Similar results were obtained when the GST moiety of the GST-PTP-OB protein fusion was cleaved with thrombin producing PTP-OB without the GST portion covalently attached.

BPs stimulate osteoblast proliferation

It was reported that orthovanadate can stimulate osteoblast proliferation. Therefore to determine whether this effect is mediated via the inhibition of PTPs, we tested whether alendronate etidronate and orthovanadate can similarly stimulate the proliferation of the mouse calvaria derived MB1.8 cells. alendronate and etidronate stimulated thymidine incorporation (mitogenesis) of quiescent osteoblasts at micromolar concentrations, demonstrating proliferation of the cells.

Requirement of PTP Activity for Bone Resorption

Figure 9A:
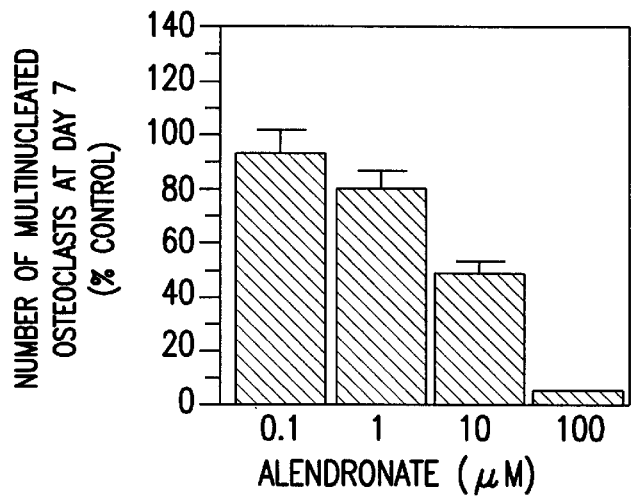
FIGS. 9A, 9B, and 9C. The inhibition of bone resorption is shown by inhibition of PTP-OB.
Figure 9B:
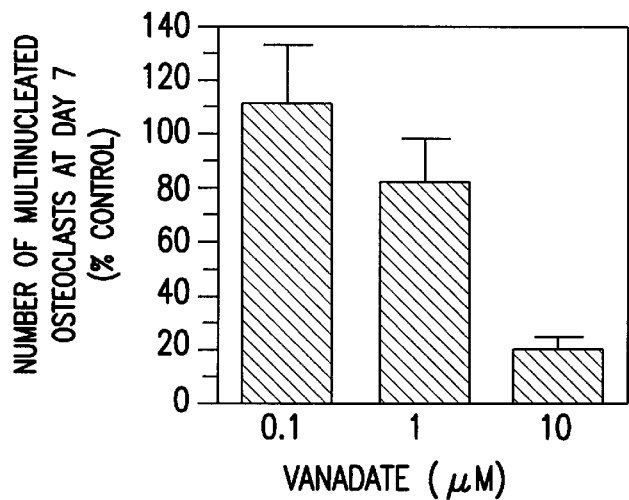
Figure 9C:
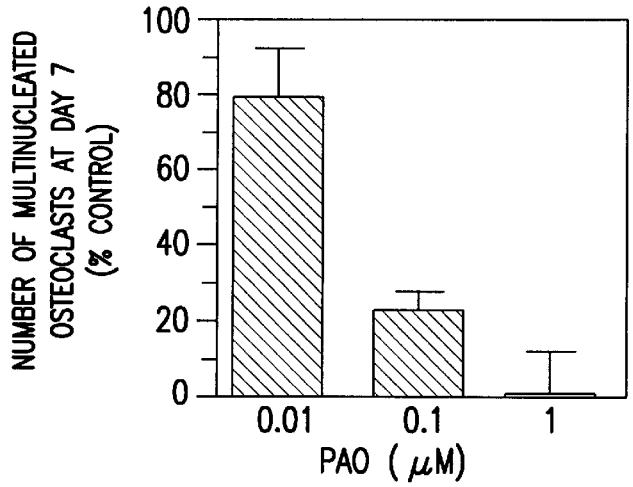

To determine a possible relationship between ALN inhibition of PTP activity and inhibition of bone resorption, we compared the effects of ALN, orthovanadate and PAO on in vitro bone resorption by rat osteoclasts. All three inhibitors (ALN, orthovanadate and PAO) inhibited the osteoclast-mediated bone resorption, reducing the number of resorption pits by 80% at $10^{-5}$M, $10^{-5}$M and $10^{-6}$M, respectively (FIG. 9). These findings suggest that PTP activity in osteoclasts is essential for bone resorption.

The Role of PTP Activity for Osteoclast Differentiation

Figure 10A:
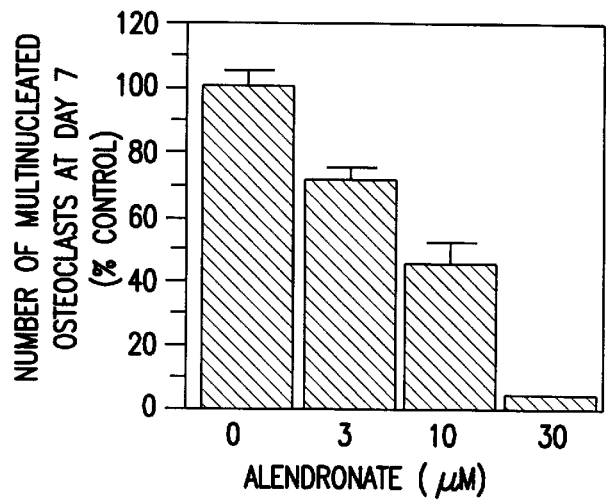
FIGS. 10A, 10B, 10C and 10D. Inhibition of formation of multinucleated TRAP positive cells by PTP inhibitors (A) alendronate, (B) orthovanadate and (C) PAO; and, (D) time course (day 1–6) inhibition of formation of multinucleated TRAP positive cells by the PTP inhibitor orthovanadate.

It has been previously reported that bisphosphonates inhibit osteoclast formation in culture [Hughes, D. E., B. R. MacDonald, R. G. Russell, and M. Gowen. 1989. Inhibition of osteoclast-like cell formation by bisphosphonates in long-term cultures of human bone marrow. J. Clin. Invest. 83:1930–1935]. We compared the effects of the three PTP inhibitors in this in vitro osteoclast formation system. Co-cultured mouse bone marrow cells and mouse calvaria osteoblasts were treated after two days with one of the PTP inhibitors, and the number of multinucleated TRAP positive cells was determined at day seven of co-culture. ALN, orthovanadate and PAO completely inhibited the formation of multinucleated TRAP positive cells at $10^{-5}$M, $10^{-5}$M and $2\times10^{-7}$M, respectively (FIG. 10A), but did not block the development of mononucleated TRAP positive cells, suggesting that the three compounds inhibit osteoclast formation at a similar step in the maturation pathway. At the respective concentrations, the three PTP inhibitors, had no apparent toxicity for either osteoblasts or bone marrow cells.

Figure 10B:
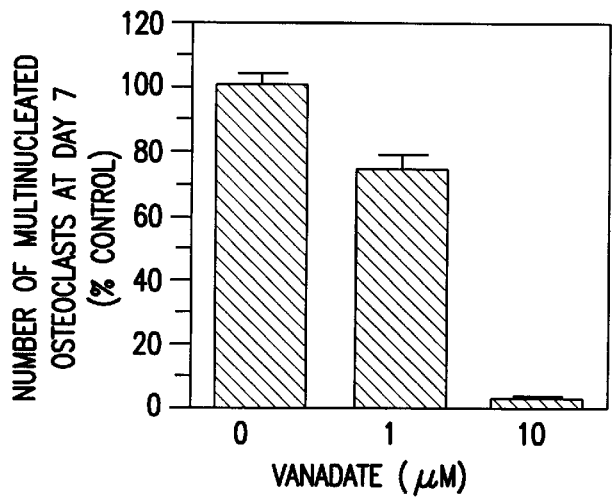
Figure 10C:
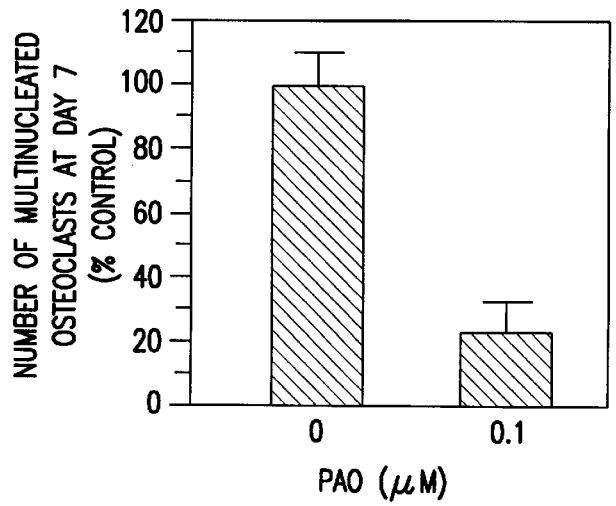
Figure 10D:
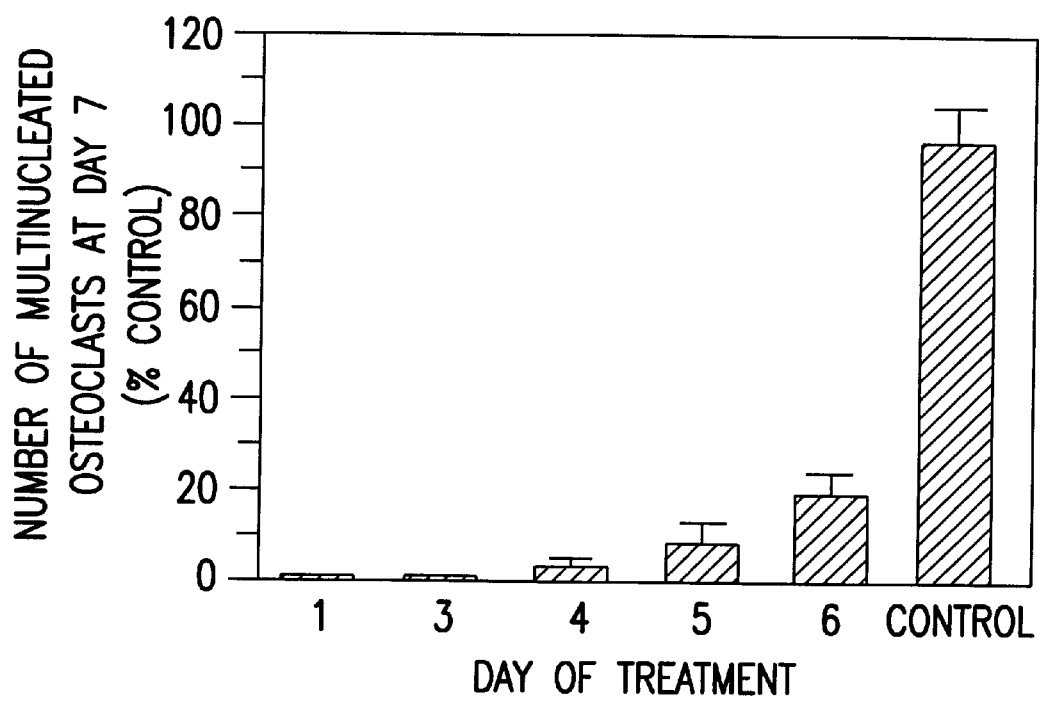

To further test the requirement for PTP activity during osteoclast formation, we added orthovanadate at different times of co-culture and counted the number of multinucleated TRAP positive cells at seven days. We found that addition of orthovanadate at any time up to day six of the co-culture inhibited the formation of multinucleated osteoclastic cells by 90% or more. Addition at day six (last 24 hours) caused 80% inhibition (FIG. 10B). These findings suggest that PTP activity is essential during a late stage in the formation of multinucleated TRAP positive cells.

Inhibition of osteoclast formation by tyrosine kinase inhibitors was recently reported [Hall, T. J., M. Schaeublin, and M. Missbach. 1994. Evidence that c-src is involved in the process of osteoclastic bone resorption. Biochem. Biophys. Res. Commun. 199:1237–1244; Yoneda, T., C. Lowe, C. H. Lee, G. Gutierrez, M. Niewolna, P. J. Williams, E. Izbicka, Y. Uehara, and G. R. Mundy, 1993. Herbimycin A, a pp60 c-src tyrosine kinase inhibitor, inhibits osteoclastic bone resorption in vitro and hypercalcemia in vivo. J. Clin. Invest. 91:2791–2795]. We found that the tyrosine kinase inhibitor, geldanamycin, also inhibited the differentiation of bone marrow cells into multinucleated TRAP positive cells, complete inhibition occurring at $2\times10^{-7}$M. However, in contrast to the effects of PTP inhibitors, geldanamycin treatment inhibited the development of mononuclear TRAP positive cells, suggesting effects at an earlier stage of osteoclast maturation.

EXAMPLE 11

Recombinant protein tyrosine phosphatase PTP-OB is expressed in a recombinant host cell (as in Examples 1–10) in native form or as a hybrid or fusion protein. PTP-OB is then used in an enzymatic assay for tyrosine phosphatase activity in a suitable buffer (0.1M TRIS-HCL, pH 7.4; 1 mM EDTA; 50 mM NaCl; 1 mM DTT). As a substrate, a phosphorylated peptide or protein is added as well as phosphorylated tyrosine or similar molecule. The release of phosphate is measured by colorimetric assay or by the release of radiolabelled phosphate. Various inhibitors are added to the assay reaction to determine their inhibitory effect on the enzymatic activity of PTP-OB. The potential inhibitor substances for use in this assay are produced synthetically or are isolated from natural sources.

What is claimed is:

1. A method of identifying a compound able to modulate protein tyrosine phosphatase activity comprising the steps of:
   a) contacting a recombinant polypeptide comprising the entire cytoplasmic domain of SEQ ID NO:5 with said compound; and
   b) measuring the ability of said compound to modulate said activity of said polypeptide.

2. The method of claim 1, further comprising the step of expressing said polypeptide from an expression vector.

3. The method of claim 2, wherein said polypeptide consists of the amino acid sequence of SEQ ID NO 5.

4. The method of claim 3, wherein said step (b) measures an increase in protein tyrosine phosphatase activity.

5. The method of claim 3, wherein said step (b) measures a decrease in protein tyrosine phosphatase activity.

6. The method of claim 3, wherein said step (b) measures protein tyrosine phosphatase activity.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CTTCTAGAAR TGYGCNCART AYTGGCC      27

(2) INFORMATION FOR SEQ ID NO:2:

(i) SEQUENCE CHARACTERISTICS:
           (A) LENGTH: 7 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:2:

Lys Cys Ala Gln Tyr Trp Pro
1               5

(2) INFORMATION FOR SEQ ID NO:3:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:3:

GAAGCTTCCM AYNCCTGCAC WRCARTGNAC                                          30

(2) INFORMATION FOR SEQ ID NO:4:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:4:

Val His Cys Ser Ala Gly Val Gly
1               5

(2) INFORMATION FOR SEQ ID NO:5:

(i) SEQUENCE CHARACTERISTICS:
           (A) LENGTH: 1911 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:5:

Met Ala Pro Thr Trp Gly Pro Gly Met Val Ser Val Gly Pro Met
1               5                  10                  15

Gly Leu Leu Val Val Leu Val Gly Gly Cys Ala Ala Glu Glu Pro
                20                  25                  30

Pro Arg Phe Ile Lys Glu Pro Lys Asp Gln Ile Gly Val Ser Gly Arg
            35                  40                  45

Val Ala Ser Phe Val Cys Gln Ala Thr Gly Asp Pro Lys Pro Arg Val
            50                  55                  60

Thr Trp Asn Lys Lys Gly Lys Lys Val Asn Ser Gln Arg Phe Glu Thr
65                  70                  75                  80

Ile Glu Phe Asp Glu Ser Ala Gly Ala Val Leu Arg Ile Gln Pro Leu
                85                  90                  95

Arg Thr Pro Arg Asp Glu Asn Val Tyr Glu Cys Val Ala Gln Asn Ser
                100                 105                 110

Val Gly Glu Ile Thr Val His Ala Lys Leu Thr Val Leu Arg Glu Asp

-continued

```
                115                 120                 125
Gln Leu Pro Ser Gly Phe Pro Asn Ile Asp Met Gly Pro Gln Leu Lys
            130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Gly Ala Leu
            180                 185                 190

Gln Ile Glu Ser Ser Glu Glu Thr Asp Gln Gly Lys Tyr Glu Cys Val
            195                 200                 205

Ala Thr Asn Ser Ala Gly Val Arg Tyr Ser Ser Pro Ala Asn Leu Tyr
            210                 215                 220

Val Arg Val Arg Arg Val Ala Pro Arg Phe Ser Ile Leu Pro Met Ser
225                 230                 235                 240

His Glu Ile Met Pro Gly Gly Asn Val Asn Ile Thr Cys Val Ala Val
                245                 250                 255

Gly Ser Pro Met Pro Tyr Val Lys Trp Met Gln Gly Ala Glu Asp Leu
                260                 265                 270

Thr Pro Glu Asp Asp Met Pro Val Gly Arg Asn Val Leu Glu Leu Thr
            275                 280                 285

Asp Val Lys Asp Ser Ala Asn Tyr His Pro Cys Val Ala Met Ser Ser
290                 295                 300

Leu Gly Val Ile Glu Ala Val Ala Gln Ile Thr Val Lys Ser Leu Pro
305                 310                 315                 320

Lys Ala Pro Gly Thr Pro Met Val Thr Glu Asn Thr Ala Thr Ser Ile
                325                 330                 335

Thr Ile Thr Trp Asp Ser Gly Asn Pro Asp Pro Val Ser Tyr Tyr Val
            340                 345                 350

Ile Glu Tyr Lys Ser Lys Ser Gln Asp Gly Pro Tyr Gln Ile Lys Glu
            355                 360                 365

Asp Ile Thr Thr Thr Arg Tyr Ser Ile Gly Gly Leu Ser Pro Asn Ser
            370                 375                 380

Glu Tyr Glu Ile Trp Val Ser Ala Val Asn Ser Ile Gly Gln Gly Pro
385                 390                 395                 400

Pro Ser Glu Ser Val Val Thr Arg Thr Gly Glu Gln Ala Pro Ala Arg
                405                 410                 415

Pro Pro Arg Asn Val Gln Ala Arg Met Leu Ser Ala Thr Thr Met Ile
            420                 425                 430

Val Gln Trp Glu Glu Pro Val Glu Pro Asn Gly Leu Ile Arg Gly Tyr
            435                 440                 445

Arg Val Tyr Tyr Thr Met Glu Pro Glu His Pro Val Gly Asn Trp Gln
450                 455                 460

Lys His Asn Val Asp Asp Ser Leu Leu Thr Thr Val Gly Ser Leu Leu
465                 470                 475                 480

Glu Asp Glu Thr Tyr Thr Val Arg Val Leu Ala Phe Thr Ser Val Gly
                485                 490                 495

Asp Gly Pro Leu Ser Asp Pro Ile Gln Val Lys Thr Gln Gln Gly Val
            500                 505                 510

Pro Gly Gln Pro Met Asn Leu Arg Ala Glu Ala Arg Ser Glu Thr Ser
            515                 520                 525

Ile Thr Leu Ser Trp Ser Pro Pro Arg Gln Glu Ser Ile Ile Lys Tyr
            530                 535                 540
```

```
Glu Leu Leu Phe Arg Glu Gly Asp His Gly Arg Glu Val Gly Arg Thr
545                 550                 555                 560

Phe Asp Pro Thr Thr Ser Tyr Val Val Glu Asp Leu Lys Pro Asn Thr
                565                 570                 575

Glu Tyr Ala Phe Arg Leu Ala Ala Arg Ser Pro Gln Gly Leu Gly Ala
            580                 585                 590

Phe Thr Pro Val Val Arg Gln Arg Thr Leu Gln Ser Lys Pro Ser Ala
            595                 600                 605

Pro Pro Gln Asp Val Lys Cys Val Ser Val Arg Ser Thr Ala Ile Leu
        610                 615                 620

Val Ser Trp Arg Pro Pro Pro Glu Thr His Asn Gly Ala Leu Val
625                 630                 635                 640

Gly Tyr Ser Val Arg Tyr Arg Pro Leu Gly Ser Glu Asp Pro Glu Pro
                645                 650                 655

Lys Glu Val Asn Gly Ile Pro Pro Thr Thr Thr Gln Ile Leu Leu Glu
                660                 665                 670

Ala Leu Glu Lys Trp Thr Gln Tyr Arg Ile Thr Thr Val Ala His Thr
            675                 680                 685

Glu Val Gly Pro Gly Pro Glu Ser Ser Pro Val Val Arg Thr Asp
690                 695                 700

Glu Asp Val Pro Ser Ala Pro Pro Arg Lys Val Glu Ala Glu Ala Leu
705                 710                 715                 720

Asn Ala Thr Ala Ile Arg Val Leu Trp Arg Ser Pro Ala Pro Gly Arg
                725                 730                 735

Gln His Gly Gln Ile Arg Gly Tyr Gln Val His Tyr Val Arg Met Glu
            740                 745                 750

Gly Ala Glu Ala Arg Gly Pro Pro Arg Ile Lys Asp Val Met Leu Ala
            755                 760                 765

Asp Ala Gln Glu Met Val Ile Thr Asn Leu Gln Pro Glu Thr Ala Tyr
            770                 775                 780

Ser Ile Thr Val Ala Ala Tyr Thr Met Lys Gly Asp Gly Ala Arg Ser
785                 790                 795                 800

Lys Pro Lys Val Val Thr Lys Gly Ala Val Leu Gly Arg Pro Thr
                805                 810                 815

Leu Ser Val Gln Gln Thr Pro Glu Gly Ser Leu Leu Ala Arg Trp Glu
                820                 825                 830

Pro Pro Ala Gly Thr Ala Glu Asp Gln Val Leu Gly Tyr Arg Leu Gln
            835                 840                 845

Phe Gly Arg Glu Asp Ser Thr Pro Leu Ala Thr Leu Glu Phe Pro Pro
850                 855                 860

Ser Glu Asp Arg Tyr Thr Ala Ser Gly Val His Lys Gly Ala Thr Tyr
865                 870                 875                 880

Val Phe Arg Leu Ala Ala Arg Ser Pro Gly Gly Leu Gly Glu Glu Ala
                885                 890                 895

Ala Glu Val Leu Ser Ile Pro Gly Asp Thr Pro Arg Gly His Pro Gln
            900                 905                 910

Ile Leu Glu Ala Ala Gly Asn Ala Ser Ala Gly Thr Val Leu Leu Arg
            915                 920                 925

Trp Leu Pro Pro Val Pro Ala Glu Arg Asn Gly Ala Ile Val Lys Tyr
        930                 935                 940

Thr Val Ala Val Arg Glu Ala Gly Ala Leu Gly Pro Ala Arg Glu Thr
945                 950                 955                 960
```

-continued

```
Glu Leu Pro Ala Gly Arg Leu Ser Arg Ala Arg Arg Thr Leu Thr Leu
            965                 970                 975

Gln Gly Leu Lys Pro Asp Thr Ala Tyr Asp Leu Gln Val Arg Ala His
            980                 985                 990

Thr Arg Arg Gly Pro Gly Pro Phe Ser Pro Val Arg Tyr Arg Thr
            995                1000                1005

Phe Leu Arg Asp Gln Val Ser Pro Lys Asn Phe Lys Val Lys Met Ile
           1010                1015                1020

Met Lys Thr Ser Val Leu Leu Ser Trp Glu Phe Pro Asp Asn Tyr Asn
1025                1030                1035                1040

Ser Pro Thr Pro Tyr Lys Ile Gln Tyr Asn Gly Leu Thr Leu Asp Val
           1045                1050                1055

Asp Gly Arg Thr Thr Lys Lys Leu Ile Thr His Leu Lys Pro His Thr
           1060                1065                1070

Phe Tyr Asn Phe Val Leu Thr Asn Arg Gly Ser Ser Leu Gly Gly Leu
           1075                1080                1085

Gln Gln Thr Val Thr Ala Trp Thr Ala Phe Asn Leu Leu Asn Gly Lys
           1090                1095                1100

Pro Ser Val Ala Pro Lys Pro Asp Ala Asp Gly Phe Ile Met Val Tyr
1105                1110                1115                1120

Leu Pro Asp Gly Gln Ser Pro Val Pro Val Gln Ser Tyr Phe Ile Val
           1125                1130                1135

Met Val Pro Leu Arg Lys Ser Arg Gly Gly Gln Phe Leu Thr Pro Leu
           1140                1145                1150

Gly Ser Pro Glu Asp Met Asp Leu Glu Glu Leu Ile Gln Asp Ile Ser
           1155                1160                1165

Arg Leu Gln Arg Arg Ser Leu Arg His Ser Arg Gln Leu Glu Val Pro
           1170                1175                1180

Arg Pro Tyr Ile Ala Ala Arg Phe Ser Val Leu Pro Pro Thr Phe His
1185                1190                1195                1200

Pro Gly Asp Gln Lys Gln Tyr Gly Gly Phe Asp Asn Arg Gly Leu Glu
           1205                1210                1215

Pro Gly His Arg Tyr Val Leu Phe Val Leu Ala Val Leu Gln Lys Ser
           1220                1225                1230

Glu Pro Thr Phe Ala Ala Ser Pro Phe Ser Asp Pro Phe Gln Leu Asp
           1235                1240                1245

Asn Pro Asp Pro Gln Pro Ile Val Asp Gly Glu Glu Gly Leu Ile Trp
           1250                1255                1260

Val Ile Gly Pro Val Leu Ala Val Phe Ile Ile Cys Ile Val Ile
1265                1270                1275                1280

Ala Ile Leu Leu Tyr Lys Asn Lys Pro Asp Ser Lys Arg Lys Asp Ser
           1285                1290                1295

Glu Pro Arg Thr Lys Cys Leu Leu Asn Asn Ala Asp Leu Ala Pro His
           1300                1305                1310

His Pro Lys Asp Pro Val Glu Met Arg Arg Ile Asn Phe Gln Thr Pro
           1315                1320                1325

Gly Met Leu Ser His Pro Pro Ile Pro Ile Ala Asp Met Ala Glu His
           1330                1335                1340

Thr Glu Arg Leu Lys Ala Asn Asp Ser Leu Lys Leu Ser Gln Glu Tyr
1345                1350                1355                1360

Glu Ser Ile Asp Pro Gly Gln Gln Phe Thr Trp Glu His Ser Asn Leu
           1365                1370                1375

Glu Val Asn Lys Pro Lys Asn Arg Tyr Ala Asn Val Ile Ala Tyr Asp
```

```
                    1380              1385              1390
His Ser Arg Val Ile Leu Gln Pro Ile Glu Gly Ile Met Gly Ser Asp
            1395              1400              1405

Tyr Ile Asn Ala Asn Tyr Val Asp Gly Tyr Arg Gln Asn Ala Tyr
    1410              1415              1420

Ile Ala Thr Gln Gly Pro Leu Pro Glu Thr Phe Gly Asp Phe Trp Arg
1425              1430              1435              1440

Met Val Trp Glu Gln Arg Ser Ala Thr Ile Val Met Met Thr Arg Leu
            1445              1450              1455

Glu Glu Lys Ser Arg Ile Lys Cys Asp Gln Tyr Trp Pro Asn Arg Gly
            1460              1465              1470

Thr Glu Thr Tyr Gly Phe Ile Gln Val Thr Leu Leu Asp Thr Ile Glu
            1475              1480              1485

Leu Ala Thr Phe Cys Val Arg Thr Phe Ser Leu His Lys Asn Gly Ser
        1490              1495              1500

Ser Glu Lys Arg Glu Val Arg Gln Phe Gln Phe Thr Ala Trp Pro Asp
1505              1510              1515              1520

His Gly Val Pro Glu Tyr Pro Thr Pro Phe Leu Ala Phe Leu Arg Arg
            1525              1530              1535

Val Lys Thr Cys Asn Pro Pro Asp Ala Gly Pro Ile Val Val His Cys
            1540              1545              1550

Ser Ala Gly Val Gly Arg Thr Gly Cys Phe Ile Val Ile Asp Ala Met
            1555              1560              1565

Leu Glu Arg Ile Lys Pro Glu Lys Thr Val Asp Val Tyr Gly His Val
            1570              1575              1580

Thr Leu Met Arg Ser Gln Arg Asn Tyr Met Val Gln Thr Glu Asp Gln
1585              1590              1595              1600

Tyr Ser Phe Ile His Glu Ala Leu Leu Glu Ala Val Gly Cys Gly Asn
            1605              1610              1615

Thr Glu Val Pro Ala Arg Ser Leu Tyr Ala Tyr Ile Gln Lys Leu Ala
            1620              1625              1630

Gln Val Glu Pro Gly Glu His Val Thr Gly Met Glu Leu Glu Phe Lys
            1635              1640              1645

Arg Leu Ala Asn Ser Lys Ala His Thr Ser Arg Phe Ile Ser Ala Asn
    1650              1655              1660

Leu Pro Cys Lys Lys Phe Lys Asn Arg Leu Val Asn Ile Met Pro Tyr
1665              1670              1675              1680

Glu Ser Thr Arg Val Cys Leu Gln Pro Ile Arg Gly Val Glu Gly Ser
            1685              1690              1695

Asp Tyr Ile Asn Ala Ser Phe Ile Asp Gly Tyr Arg Gln Gln Lys Ala
            1700              1705              1710

Tyr Ile Ala Thr Gln Gly Pro Leu Ala Glu Thr Thr Glu Asp Phe Trp
            1715              1720              1725

Arg Met Leu Trp Glu Asn Asn Ser Thr Ile Val Val Met Leu Thr Lys
    1730              1735              1740

Leu Arg Glu Met Gly Arg Glu Lys Cys His Gln Tyr Trp Pro Ala Glu
1745              1750              1755              1760

Arg Ser Ala Arg Tyr Gln Tyr Phe Val Val Asp Pro Met Ala Glu Tyr
            1765              1770              1775

Asn Met Pro Gln Tyr Ile Leu Arg Glu Phe Lys Val Thr Asp Ala Arg
            1780              1785              1790

Asp Gly Gln Ser Arg Thr Val Arg Gln Phe Gln Phe Thr Asp Trp Pro
            1795              1800              1805
```

```
Glu Gln Gly Val Pro Lys Ser Gly Glu Gly Phe Ile Asp Phe Ile Gly
    1810            1815                1820
Gln Val His Lys Thr Lys Glu Gln Phe Gly Gln Asp Gly Pro Ile Ser
1825            1830                1835                1840
Val His Cys Ser Ala Gly Val Gly Arg Thr Gly Val Phe Ile Thr Leu
            1845                1850                1855
Ser Ile Val Leu Glu Arg Met Arg Tyr Glu Gly Val Val Asp Ile Phe
            1860                1865                1870
Gln Thr Val Lys Met Leu Arg Thr Gln Arg Pro Ala Met Val Gln Thr
            1875                1880                1885
Glu Asp Glu Tyr Gln Phe Cys Tyr Gln Ala Ala Leu Glu Tyr Leu Gly
    1890                1895                1900
Ser Phe Asp His Tyr Ala Thr
1905            1910

(2) INFORMATION FOR SEQ ID NO:6:

(i) SEQUENCE CHARACTERISTICS:
        (A) LENGTH: 6000 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GAATTCCGGG TCGCTGCCAA GCATGGCGCC CACCTGGGGC CCTGGCATGG TGTCTGTGGT     60
TGGTCCCATG GGCCTCCTTG TGGTCCTGCT CGTTGGAGGC TGTGCAGCAG AAGAGCCCCC    120
CAGGTTTATC AAAGAACCCA AGGACCAGAT CGGCGTGTCG GGGCGTGTGG CCTCTTTCGT    180
GTGTCAGGCC ACGGGTGACC CCAAGCCACG AGTGACCTGG AACAAGAAGG CAAGAAGGT    240
CAACTCTCAG CGCTTTGAGA CGATTGAGTT TGATGAGAGT GCAGGGGCAG TGCTGAGGAT    300
CCAGCCGCTG AGGACACCGC GGGATGAAAA CGTGTACGAG TGTGTGGCCC AGAACTCGGT    360
TGGGGAGATC ACAGTCCATG CCAAGCTTAC TGTCCTCCGA GAGGACCAGC TGCCCTCTGG    420
CTTCCCCAAC ATCGACATGG CCCACAGTT GAAGGTGGTG GAGCGGACAC GGACAGCCAC    480
CATGCTCTGT GCAGCCAGCG GCAACCCTGA CCCTGAGATC ACCTGGTTCA AGGACTTCCT    540
GCCTGTGGAT CCTAGTGCCA GCAATGGACG CATCAAACAG CTGCGATCAG GAGCCCTGCA    600
GATTGAAAGC AGTGAGGAAA CCGACCAGGG CAAATATGAG TGTGTGGCCA CCAACAGCGC    660
CGGCGTGCGC TACTCCTCAC CTGCCAACCT CTACGTGCGA GTCCGCCGCG TGGCCCCGCG    720
CTTCTCCATC CTGCCCATGA GCCACGAGAT CATGCCAGGG GCAACGTGA ACATCACCTG    780
CGTGGCCGTG GGCTCGCCCA TGCCATACGT GAAGTGGATG CAGGGGGCCG AGGACCTGAC    840
CCCCGAGGAT GACATGCCCG TGGGTCGGAA CGTGCTGGAA CTCACAGATG TCAAGGACTC    900
GGCCAACTAC CACCCCTGCG TGGCCATGTC CAGCCTGGGC GTCATTGAGG CGGTTGCTCA    960
GATCACGGTG AAATCTCTCC CCAAAGCTCC CGGGACTCCC ATGGTGACTG AGAACACAGC   1020
CACCAGCATC ACCATCACGT GGGACTCGGG CAACCCAGAT CCTGTGTCCT ATTACGTCAT   1080
CGAATATAAA TCCAAGAGCC AAGACGGGCC GTATCAGATT AAAGAGGACA TCACCACCAC   1140
ACGTTACAGC ATCGGCGGCC TGAGCCCCAA CTCGGAGTAC GAGATCTGGG TGTCGGCCGT   1200
CAACTCCATC GGCCAGGGGC CCCCAGCGA GTCCGTGGTC ACCCGCACAG GCGAGCAGGC   1260
CCCGGCCAGG CCGCCGCGGA ACGTGCAAGC CCGGATGCTC AGCGCGACCA CCATGATTGT   1320
```

```
GCAGTGGGAG GAGCCGGTGG AGCCCAACGG CCTGATCCGC GGCTACCGCG TCTACTACAC    1380

CATGGAACCG GAGCACCCCG TGGGCAACTG GCAGAAGCAC AACGTGGACG ACAGCCTGCT    1440

GACCACCGTG GGCAGCCTGC TGGAGGACGA GACCTACACC GTGCGGGTGC TCGCCTTCAC    1500

CTCCGTCGGC GACGGGCCCC TCTCGGACCC CATCCAGGTC AAGACGCAGC AGGGAGTGCC    1560

GGGCCAGCCC ATGAACCTGC GGGCCGAGGC CAGGTCGGAG ACCAGCATCA CGCTGTCCTG    1620

GAGCCCCCCG CGGCAGGAGA GTATCATCAA GTACGAGCTC CTCTTCCGGG AAGGCGACCA    1680

TGGCCGGGAG GTGGGAAGGA CCTTCGACCC GACGACTTCC TACGTGGTGG AGGACCTGAA    1740

GCCCAACACG GAGTACGCCT TCCGCCTGGC GGCCCGCTCG CCGCAGGGCC TGGGCGCCTT    1800

CACCCCCGTG GTGCGGCAGC GCACGCTGCA GTCCAAACCG TCAGCCCCCC CTCAAGACGT    1860

TAAATGTGTC AGCGTGCGCT CCACGGCCAT TTTGGTAAGT TGGCGCCCGC CGCCGCCGGA    1920

AACGCACAAC GGGGCCCTGG TGGGCTACAG CGTCCGCTAC CGACCGCTGG GCTCAGAGGA    1980

CCCGGAACCC AAGGAGGTGA ACGGCATCCC CCCGACCACC ACTCAGATCC TGCTGGAGGC    2040

CTTGGAGAAG TGGACCCAGT ACCGCATCAC GACTGTCGCT CACACAGAGG TGGGACCAGG    2100

GCCCGAGAGC TCGCCCGTGG TCGTCCGCAC CGACGAGGAT GTGCCCAGCG CGCCGCCGCG    2160

GAAGGTGGAG GCGGAGGCGC TCAACGCCAC GGCCATCCGC GTGCTGTGGC GCTCGCCCGC    2220

GCCCGGCCGG CAGCACGGCC AGATCCGCGG CTACCAGGTC CACTACGTGC GCATGGAGGG    2280

CGCCGAGGCC CGCGGGCCGC CGCGCATCAA GGACGTCATG CTGGCCGATG CCCAGGAGAT    2340

GGTCATCACA AACTTGCAGC CTGAGACCGC GTACTCCATC ACGGTAGCCG CCTACACCAT    2400

GAAGGGCGAT GGCGCTCGCA GCAAACCCAA GGTGGTTGTG ACCAAGGGAG CAGTGCTGGG    2460

CCGCCCAACC CTGTCGGTGC AGCAGACCCC CGAGGGCAGC CTGCTGGCAC GCTGGGAGCC    2520

CCCGGCTGGC ACCGCGGAGG ACCAGGTGCT GGGCTACCGC CTGCAGTTTG CCGTGAGGA    2580

CTCGACGCCC CTGGCCACCC TGGAGTTCCC GCCCTCCGAG GACCGCTACA CGGCATCAGG    2640

CGTGCACAAG GGGGCCACGT ATGTGTTCCG GCTTGCGGCC GGAGCCCGG GCGGCCTGGG    2700

CGAGGAGGCA GCCGAGGTCC TGAGCATCCC GGAGGACACG CCCCGTGGCC ACCCGCAGAT    2760

TCTGGAGGCG GCCGGCAACG CCTCGGCCGG GACCGTCCTT CTCCGCTGGC TGCCACCCGT    2820

GCCCGCCGAG CGCAACGGGG CCATCGTCAA ATACACGGTG GCCGTGCGGG AGGCCGGTGC    2880

CCTGGGCCCT GCCCGAGAGA CTGAGCTGCC GGCAGGCCGG CTGAGCCGGG CGCGGAGAAC    2940

GCTCACGCTG CAGGGCCTGA AGCCCGACAC GGCCTATGAC CTCCAAGTGC GAGCCCACAC    3000

GCGCCGGGGC CCTGGCCCCT TCAGCCCCCC CGTCCGCTAC CGGACGTTCC TGCGGGACCA    3060

AGTCTCGCCC AAGAACTTCA AGGTGAAAAT GATCATGAAG ACATCAGTTC TGCTCAGCTG    3120

GGAGTTCCCT GACAACTACA ACTCACCCAC ACCCTACAAG ATCCAGTACA ATGGGCTCAC    3180

ACTGGATGTG GATGGCCGTA CCACCAAGAA GCTCATCACG CACCTCAAGC CCACACCTT    3240

CTACAACTTT GTGCTGACCA ATCGCGGCAG CAGCCTGGGC GGCCTCCAGC AGACGGTCAC    3300

CGCCTGGACT GCCTTCAACC TGCTCAACGG CAAGCCCAGC GTCGCCCCCA AGCCTGATGC    3360

TGACGGCTTC ATCATGGTGT ATCTTCCTGA CGGCCAGAGC CCCGTGCCTG TCCAGAGCTA    3420

TTTCATTGTG ATGGTGCCAC TGCGCAAGTC TCGTGGAGGC CAATTCCTGA CCCCGCTGGG    3480

TAGCCCAGAG GACATGGATC TGGAAGAGCT CATCCAGGAC ATCTCACGGC TACAGAGGCG    3540

CAGCCTGCGG CACTCGCGTC AGCTGGAGGT GCCCCGGCCC TATATTGCAG CTCGCTTCTC    3600

TGTGCTGCCA CCCACGTTCC ATCCCGGCGA CCAGAAGCAG TATGGCGGCT TCGATAACCG    3660

GGGCCTGGAG CCCGGCCACC GCTATGTCCT CTTCGTGCTT GCCGTGCTTC AGAAGAGCGA    3720
```

-continued

```
GCCTACCTTT GCAGCCAGTC CCTTCTCAGA CCCCTTCCAG CTGGATAACC CGGACCCCCA    3780

GCCCATCGTG GATGGCGAGG AGGGGCTTAT CTGGGTGATC GGGCCTGTGC TGGCCGTGGT    3840

CTTCATAATC TGCATTGTCA TTGCTATCCT GCTCTACAAG AACAAACCCG ACAGTAAACG    3900

CAAGGACTCA GAACCCCGCA CCAAATGCCT CCTGAACAAT GCCGACCTCG CCCCTCACCA    3960

CCCCAAGGAC CCTGTGGAAA TGAGACGCAT TAACTTCCAG ACTCCAGGCA TGCTTAGCCA    4020

CCCGCCAATT CCCATCGCAG ACATGGCGGA GCACACGGAG CGGCTCAAGG CCAACGACAG    4080

CCTCAAGCTC TCCCAGGAGT ATGAGTCCAT CGACCCTGGA CAGCAGTTCA CATGGGAACA    4140

TTCCAACCTG GAAGTGAACA AGCCGAAGAA CCGCTATGCC AACGTCATCG CCTATGACCA    4200

CTCCCGTGTC ATCCTCCAGC CCATTGAAGG CATCATGGGC AGTGATTACA TCAATGCCAA    4260

CTACGTGGAC GGCTACCGGC GTCAGAACGC GTACATTGCC ACGCAGGGGC CGCTGCCTGA    4320

GACCTTTGGG GACTTCTGGC GTATGGTGTG GGAGCAGCGG TCGGCGACCA TCGTCATGAT    4380

GACGCGGCTG GAGGAGAAGT CACGGATCAA GTGTGATCAG TATTGGCCCA ACAGAGGCAC    4440

GGAGACCTAC GGCTTCATCC AGGTCACGTT GCTAGATACC ATCGAGCTGG CCACATTCTG    4500

CGTCAGGACA TTCTCTCTGC ACAAGAATGG CTCCAGTGAG AAACGCGAGG TCCGCCAGTT    4560

CCAGTTTACG GCGTGGCCGG ACCATGGCGT GCCCGAATAC CCAACGCCCT TCCTGGCTTT    4620

CCTGCGGAGA GTCAAGACCT GCAACCCACC AGATGCCGGC CCCATCGTGG TTCACTGCAG    4680

TGCCGGTGTG GGCCGCACAG GCTGCTTTAT CGTCATCGAC GCCATGCTTG AGCGGATCAA    4740

GCCAGAGAAG ACAGTCGATG TCTATGGCCA CGTGACGCTC ATGAGGTCCC AGCGCAACTA    4800

CATGGTGCAG ACGGAGGACC AGTACAGCTT CATCCACGAG GCCCTGCTGG AGGCCGTGGG    4860

CTGTGGCAAC ACAGAAGTGC CCGCACGCAG CCTCTATGCC TACATCCAGA AGCTGGCCCA    4920

GGTGGAGCCT GGCGAACACG TCACTGGCAT GGAACTCGAG TTCAAGCGGC TGGCTAACTC    4980

CAAGGCCCAC ACGTCACGCT TCATCAGTGC CAATCTGCCT TGTAAGAAGT TCAAGAACCG    5040

CCTGGTGAAC ATCATGCCCT ATGAGAGCAC ACGGGTCTGT CTGCAACCCA TCCGGGGTGT    5100

GGAGGGCTCT GACTACATCA ACGCCAGCTT CATTGATGGC TACAGGCAGC AGAAGGCCTA    5160

CATCGCGACA CAGGGGCCGC TGGCGGAGAC CACGGAAGAC TTCTGGCGCA TGCTGTGGGA    5220

GAACAATTCG ACGATCGTGG TGATGCTGAC CAAGCTGCGG GAGATGGGCC GGGAGAAGTG    5280

TCACCAGTAC TGGCCGGCCG AGCGCTCTGC CCGCTACCAG TACTTTGTGG TAGATCCGAT    5340

GGCAGAATAC AACATGCCTC AGTATATCCT GCGAGAGTTC AAGGTCACAG ATGCCCGGGA    5400

TGGCCAGTCC CGGACTGTCC GGCAGTTCCA GTTCACAGAC TGGCCGGAAC AGGGTGTGCC    5460

AAAGTCGGGG GAGGGCTTCA TCGACTTCAT TGGCCAAGTG CATAAGACTA AGGAGCAGTT    5520

TGGCCAGGAC GGCCCCATCT CTGTCCACTG CAGTGCCGGC GTGGGCAGGA CGGGCGTCTT    5580

CATCACGCTT AGCATCGTGC TGGAGCGGAT GCGGTATGAA GGCGTGGTGG ACATCTTTCA    5640

GACGGTGAAG ATGCTACGAA CCCAGCGGCC GGCCATGGTG CAGACAGAGG ATGAGTACCA    5700

GTTCTGTTAC CAGGCGGCAC TGGAGTACCT CGGAAGCTTT GACCACTATG CAACCTAAAG    5760

CCATGGTCCC CCCCAGGCCC GACACCACTG GCCCCGGATG CCTCTGCCCC TCCCGGGCGG    5820

ACCTCCTGAG GCCTGGACCC CCAGTGGGCA GGGCAGGAGG TGGCAGCGGC AGCAGCTGTG    5880

TTTCTGCACC ATTTCCGAGG ACGACGCAGC CCCTCGAGCC CCCCACCGG CCCCGGCCGC    5940

CCCAGCGACC TCCCTGGCAC GGCCGCCGCC TTCAAATACT GGCACATTC CCCGAATTC    6000
```

(2) INFORMATION FOR SEQ ID NO:7:

(i) SEQUENCE CHARACTERISTICS:
        (A) LENGTH: 699 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Met Glu Pro Phe Cys Pro Leu Leu Ala Ser Phe Leu Ser Leu
1               5                   10                  15

Ala Arg Ala Gly Gln Gly Asn Asp Thr Thr Pro Thr Glu Ser Asn Trp
            20                  25                  30

Thr Ser Thr Thr Ala Gly Pro Pro Asp Pro Gly Ala Ser Gln Pro Leu
        35                  40                  45

Leu Thr Trp Leu Leu Leu Pro Leu Leu Leu Leu Phe Leu Leu Ala
    50                  55                  60

Ala Tyr Phe Phe Arg Phe Arg Lys Gln Arg Lys Ala Val Val Ser Ser
65              70                  75                  80

Asn Asp Lys Lys Met Pro Asn Gly Ile Leu Glu Glu Gln Glu Gln Gln
                85                  90                  95

Arg Val Met Leu Leu Ser Arg Ser Pro Ser Gly Pro Lys Lys Phe Phe
            100                 105                 110

Pro Ile Pro Val Glu His Leu Glu Glu Glu Ile Arg Val Arg Ser Ala
        115                 120                 125

Asp Asp Cys Lys Arg Phe Arg Glu Glu Phe Asn Ser Leu Pro Ser Gly
130                 135                 140

His Ile Gln Gly Thr Phe Glu Leu Ala Asn Lys Glu Glu Asn Arg Glu
145                 150                 155                 160

Lys Asn Arg Tyr Pro Asn Ile Leu Pro Asn Asp His Cys Arg Val Ile
                165                 170                 175

Leu Ser Gln Val Asp Gly Ile Pro Cys Ser Asp Tyr Ile Asn Ala Ser
            180                 185                 190

Tyr Ile Asp Gly Tyr Lys Glu Lys Asn Lys Phe Ile Ala Ala Gln Gly
        195                 200                 205

Pro Lys Gln Glu Thr Val Asn Asp Phe Trp Arg Met Val Trp Glu Gln
210                 215                 220

Arg Ser Ala Thr Ile Val Met Leu Thr Asn Leu Lys Glu Arg Lys Glu
225                 230                 235                 240

Glu Lys Cys Tyr Gln Tyr Trp Pro Asp Gln Gly Cys Trp Thr Tyr Gly
                245                 250                 255

Asn Ile Arg Val Cys Val Glu Asp Cys Val Val Leu Val Asp Tyr Thr
            260                 265                 270

Ile Arg Lys Phe Cys Ile His Pro Gln Leu Pro Asp Ser Cys Lys Ala
        275                 280                 285

Pro Arg Leu Val Ser Gln Leu His Phe Thr Ser Trp Pro Asp Phe Gly
290                 295                 300

Val Pro Phe Thr Pro Ile Gly Met Leu Lys Phe Leu Lys Lys Val Lys
305                 310                 315                 320

Thr Leu Asn Pro Ser His Ala Gly Pro Ile Val Val His Cys Ser Ala
                325                 330                 335

Gly Val Gly Arg Thr Gly Thr Phe Ile Val Ile Asp Ala Met Met Asp
            340                 345                 350

Met Ile His Ser Glu Gln Lys Val Asp Val Phe Glu Phe Val Ser Arg
        355                 360                 365

-continued

```
Ile Arg Asn Gln Arg Pro Gln Met Val Gln Thr Asp Val Gln Tyr Thr
    370                 375                 380
Phe Ile Tyr Gln Ala Leu Leu Glu Tyr Tyr Leu Tyr Gly Asp Thr Glu
385                 390                 395                 400
Leu Asp Val Ser Ser Leu Glu Arg His Leu Gln Thr Leu His Ser Thr
                405                 410                 415
Ala Thr His Phe Asp Lys Ile Gly Leu Glu Glu Phe Arg Lys Leu
                420                 425                 430
Thr Asn Val Arg Ile Met Lys Glu Asn Met Arg Thr Gly Asn Leu Pro
            435                 440                 445
Ala Asn Met Lys Lys Ala Arg Val Ile Gln Ile Ile Pro Tyr Asp Phe
    450                 455                 460
Asn Arg Val Ile Leu Ser Met Lys Arg Gly Gln Glu Phe Thr Asp Tyr
465                 470                 475                 480
Ile Asn Ala Ser Phe Ile Asp Gly Tyr Arg Gln Lys Asp Tyr Phe Met
                485                 490                 495
Ala Thr Gln Gly Pro Leu Ala His Thr Val Glu Asp Phe Trp Arg Met
                500                 505                 510
Val Trp Glu Trp Lys Ser His Thr Ile Val Met Leu Thr Glu Val Gln
            515                 520                 525
Glu Arg Glu Gln Asp Lys Cys Tyr Gln Tyr Trp Pro Thr Glu Gly Ser
    530                 535                 540
Val Thr His Gly Asp Ile Thr Ile Glu Ile Lys Ser Asp Thr Leu Ser
545                 550                 555                 560
Glu Ala Ile Ser Val Arg Asp Phe Leu Val Thr Phe Lys Gln Pro Leu
                565                 570                 575
Ala Arg Gln Glu Glu Gln Val Arg Met Val Arg Gln Phe His Phe His
                580                 585                 590
Gly Trp Pro Glu Val Gly Ile Pro Ala Glu Gly Lys Gly Met Ile Asp
            595                 600                 605
Leu Ile Ala Ala Val Gln Lys Gln Gln Gln Thr Gly Asn His Pro
    610                 615                 620
Ile Thr Val His Cys Ser Ala Gly Ala Gly Arg Thr Gly Thr Phe Ile
625                 630                 635                 640
Ala Leu Ser Asn Ile Leu Glu Arg Val Lys Ala Glu Gly Leu Leu Asp
                645                 650                 655
Val Phe Gln Ala Val Lys Ser Leu Arg Leu Gln Arg Pro His Met Val
                660                 665                 670
Gln Thr Leu Glu Gln Tyr Glu Phe Cys Tyr Lys Val Val Gln Asp Phe
            675                 680                 685
Ile Asp Ile Phe Ser Asp Tyr Ala Asn Phe Lys
    690                 695
```